US011692024B2

United States Patent
Kinney et al.

(10) Patent No.: US 11,692,024 B2
(45) Date of Patent: Jul. 4, 2023

(54) METHODS OF TREATING AL AMYLOIDOSIS

(71) Applicant: PROTHENA BIOSCIENCES LIMITED, Dublin (IE)

(72) Inventors: Gene Kinney, Boca Raton, FL (US); Carol Karp, Hillsborough, CA (US); Wagner Marcelo Zago, San Carols, CA (US); Radhika Tripuraneni, San Francisco, CA (US)

(73) Assignee: Prothena Biosciences Limited, Dublin (IE)

( * ) Notice: Subject to any disclaimer, the term of this patent is extended or adjusted under 35 U.S.C. 154(b) by 0 days.

(21) Appl. No.: 16/810,319

(22) Filed: Mar. 5, 2020

(65) Prior Publication Data
US 2020/0308260 A1    Oct. 1, 2020

Related U.S. Application Data

(60) Provisional application No. 62/942,722, filed on Dec. 2, 2019, provisional application No. 62/814,252, filed on Mar. 5, 2019.

(51) Int. Cl.
| | |
|---|---|
| C07K 16/18 | (2006.01) |
| A61B 5/0205 | (2006.01) |
| A61K 9/00 | (2006.01) |
| A61K 39/395 | (2006.01) |
| A61B 5/029 | (2006.01) |
| A61B 5/00 | (2006.01) |
| A61K 45/06 | (2006.01) |
| A61B 5/11 | (2006.01) |

(52) U.S. Cl.
CPC ............ *C07K 16/18* (2013.01); *A61B 5/0205* (2013.01); *A61B 5/4839* (2013.01); *A61B 5/4842* (2013.01); *A61K 9/0019* (2013.01); *A61K 39/3955* (2013.01); *A61K 45/06* (2013.01); *A61B 5/029* (2013.01); *A61B 5/1124* (2013.01); *C07K 2317/24* (2013.01); *C07K 2317/565* (2013.01)

(58) Field of Classification Search
CPC .. C07K 16/18; C07K 2317/24; A61B 5/0205; A61K 9/0019
See application file for complete search history.

(56) References Cited

U.S. PATENT DOCUMENTS

| | | | |
|---|---|---|---|
| 7,829,673 | B2 | 11/2010 | DeWeers et al. |
| 7,928,203 | B2 | 4/2011 | Schenk et al. |
| 8,105,594 | B2 | 1/2012 | Solomon et al. |
| 8,263,746 | B2 | 9/2012 | Tesar et al. |
| 9,089,529 | B2 | 7/2015 | Garidel et al. |
| 9,249,226 | B2 | 2/2016 | DeWeers et al. |
| 9,364,542 | B2 | 6/2016 | Chang |
| 9,884,020 | B2 | 2/2018 | Garidel et al. |
| 10,046,050 | B2 | 8/2018 | Wall et al. |
| 10,766,965 | B2 | 9/2020 | Chaulagin et al. |
| 2017/0008966 | A1 | 1/2017 | Chaulagin et al. |
| 2017/0121414 | A1 | 5/2017 | Jansson et al. |
| 2019/0038745 | A1 | 2/2019 | Lentzsch et al. |
| 2020/0002410 | A1 | 1/2020 | Lentzsch et al. |
| 2022/0213223 | A1 | 7/2022 | Comenzo et al. |

FOREIGN PATENT DOCUMENTS

| | | |
|---|---|---|
| WO | WO 2002/060919 | 8/2002 |
| WO | WO 2009/086539 | 7/2009 |
| WO | WO 2013/063284 | 5/2013 |
| WO | WO 2016/187546 | 11/2016 |
| WO | WO 2018/005967 | 1/2018 |

OTHER PUBLICATIONS

Gertz et al., "Results of the Phase 3 VITAL Study of NEOD001 (Birtamimab) Plus Standard of Care in Patients with Light Chain (AL) Amyloidosis Suggest Survival Benefit for Mayo Stage IV Patients" Blood 134(Suppl. 1):3116 (Nov. 13, 2019). 8 pages.

Merlin et al., "Systemic immunoglobulin light chain amyloidosis" Nature Reviews Disease Primers, vol. 4, No. 1, pp. 1-19 (Oct. 25, 2018).

Muchtar et al., "Clinical trials evaluating potential therapies for light chain (AL) amyloidosis", Expert Opinion on Orphan Drugs, vol. 5, No. 8, pp. 655-663 (Jun. 19, 2017).

Shen et al., "Bortezomib-Based Chemotherapy Reduces Early Mortality and Improves Outcomes in Patients with Ultra-High-Risk Light-Chain Amyloidosis" Blood, 132(Suppl. 1):3304 (Nov. 29, 2018). 5 pages.

Vaxman et al., "New developments in diagnosis, risk assessment and management in systemic amyloidosis", Blood Reviews, vol. 40, (2020) pp. 1-13 (Nov. 2, 2019).

The International Search Report for International Application No. PCT/IB2020/000186; dated Jul. 7, 2020, pp. 1-6.

NCT02312206—The VITAL Amyloidosis Study, a Global Phase 3, Efficacy and Safety Study of NEOD001 in Patients with AL Amyloidosis (VITAL).—first posted Dec. 9, 2014, pp. 1-28.

The PRONTO Study, a Global Phase 2b Study of NEOD001 in Previously Treated Subjects With Light Chain (AL) Amyloidosis (PRONTO), first posted Dec. 17, 2015, pp. 1-31.

Prothena Discontinues Development of NEOD001 for AL Amyloidosis, press release, Apr. 23, 2018.

Agis, H., "News in AL Amyloidosis ASH 2016, A rapidly evolving field of investigation", Memo, 10:66-71 (2017).

Cordes, S., et al., "Ten-Year Survival After Autologous Stem Cell Transplantation for Immunoglobulin Light Chain Amyloidosis", Cancer, 118:6105-6109 (2012).

Dispenzieri, A., et al., "High sensitivity cardiac troponin T in patients with immunoglobulin light chain amyloidosis", Heart, 100:383-388 (2014).

Dispenzieri, A., et al., "Treatment of Immunoglobulin Light Chain Anyloidosis: Mayo Stratification of Myeloma and Risk-Adapted Therapy (mSmart) Consensus Statement", Mayo Clin Proc. 90:1054-1081 (2015).

Gertz, M., et al,. "Refinement in patient selection to reduce treatment-related mortality from autologous stem cell transplantation in amyloidosis", Bone Marrow Transplantation, 48:557-561 (2013).

(Continued)

*Primary Examiner* — Olga N Chernyshev
(74) *Attorney, Agent, or Firm* — Fish & Richardson P.C.

(57) ABSTRACT

Antibody formulations and methods useful for treatment of patients with AL amyloidosis.

42 Claims, 7 Drawing Sheets

Specification includes a Sequence Listing.

(56) References Cited

OTHER PUBLICATIONS

Gertz, M., et al., "Autologous stem cell transplant for immunoglobulin light chain amyloidosis: a stuatus report", Leukemia & Lymphoma, 51: 2181-2187 (2010).
Gertz, M., et al., "First-in-Human Phase I/II Study of NEOD001 in Patients with Light Chain Amyloidosis and Presistent Organ Dysfunction", Journal of Clinical Oncology, 34:1097-1103 (2016).
Gertz, M., et al., "NEOD001 Demonstrates Organ Biomarker Responses in Patient with Light Chain Amyloidosis and Persistent Organ Dysfunction: Results from the Expansion Cohort of a Phase 1/2 Study", Blood, 128:1-4 (2016).
Gertz, et al., "Organ response in patients with AL amyloidosis treated with NEOD001, an amyloid-directedmonoclonal antibody", American Journal of Hematology, 91:E506-E508 (2016).
Godara, A., et al., "Dual Monoclonal Antibody Therapy in Patients with Systemic AL Amyloidosis and Cardiac Involvement", Clinical Lymphoma, Myeloma & Leukemia, 20:184-189 (2019).
Joseph, N., et al., "Novel Approaches for the Management of AL Amyloidosis", Current Hematologic Malignancy Reports, 13:212-219 (2018).
Kastritis, E., et al., "Clinical and prognostic significance of serum levels of von Willebrand tractor and ADAMTS-13 antigens in AL amyloidosis", Blood, 128:405-409 (2016).
Kaufman, G., et al., "Beyond Andromeda: Improving Therapy for Light Chain Amyloidosis", Frontiers in Oncology, 10:1-5 (2021).
Kristen, A., et al., "Assessment of disease severity and outcome in patients with systemic light-chaim amyloidosis by the high-sensitivity troponin T assay", Blood, 116:2455-2461 (2010).
Kumar, S., et al., "Recent Improvements in Survival in Primary Systemic Amyloidosis and the Importance of an Early Mortality Risk Score", Mayo Clin Proc., 86:12-18 (2011).
Lee, J., et al., "Bortezomib, melphalan, and prednisolone combination chemotherapy for newly diagnosed light chain (AL) amyloidosis", Amyloid, pp. 1-6 (2014).
Liedtke, M., et al., "NEOD001 Demonstrates Cardiac Biomarker Responses in Patients with Light Chain Amyloidosis: Results from the Phase 1/2 Study", JACC, 69,11 (2017).
Liedtke, M., et al., "Organ Biomarker Responses in Patients with Light Chain Amyloidosis Treated with NEOD001 Are Independent of Previous Hematologic Response", Blood, 128:1-4 (2016).
Liedtke, M., et al., "The VITAL Amyloidosis Study: A Randomized, Double-Blind, Placebo-Controlled, Global, Phase 3 Study of NEOD001 in Patients with AL Amyloidosis and Cardiac Dysfunction", Blood, 128:1-3 (2016).
Muchtar, E., et al., "Clinical trials evaluating potential therapies for light chain (AL) amyloidosis", Expert Opin Orphan Drugs, 5:655-663 (2017).
Popkova, T., et al., "Monoclonal antibodies in the treatment of AL amyloidosis: co-targetting the plasma cell clone and amyloid deposits", British Journal of Haematology, 189:228-238 (2020).
Pun, S., et al., "Prognostic and Added Value of Two-Dimensional Global Longitudinal Strain for Prediction of Survival in Patients with Light Chain Amyloidosis Undergoing Autologous Hematopoietic Cell Transplantation", Journal of the American Society of Echocardiography (2017).
Renz, M., et al., "2A4 binds soluble and insoluble light chain aggregates from AL amyloidosis patients and promotes clearance of amyloid deposits by phagocytosis", Amyloid, Early Online: 1-10 (2016).
Sperry, B., et al., "Efficacy of Chemotherapy for Light-Chain Amyloidosis in Patients Presenting With Symptomatic Heart Failure", J Am Coll Cardiol., 67:2941-2948 (2016).
Van Doren, L., et al., "Nonchemotherapy Treatment of Immunoglobulin Light Chain Amyloidosis", Acta Haematologica, 143:373-380 (2020).
Varga, C., et al., "Beyond NEOD001 for Systemic Light-chain Amyloidosis", Blood, 865857 (2018).
Venner, C., et al., "Cyclophosphamide, bortezomib, and dexamthasone therapy in AL amyloidosis is associated with high clonal response rates and prolonged progression-free survival", Blood, 119:4387-4390 (2012).
Wall, J., et al., "AL Amyloid Imaging and Therapy with a Monoclonal Antibody to a Cryptic Epitope on Amyloid Fibrils", PLoS One, 7:1-10 (2012).
Wall, J., et al., "Generation and characterization of anti-AA amyloid-specific monoclonal antibodies", Frontiers in Immunology, 2:1-11 (2011).
Warsame, et al., "Hematology patient reported symptom screen to assess quality of life for AL amyloidosis", Am J Hematol., 92:435-440 (2017).
Zago, W., et al., "NEOD001 Specifically Binds Aggregated Light Chain Infiltrates in Multiple Organs with Patients with AL Amyloidosis and Promotes Phagocytic Clearance of AL Aggregates in Vitro", Blood, 126:1-5 (2015).
Abeykoon et al., "Daratumumab-based therapy in patients with heavily-pretreated AL amyloidosis", Sep. 28, 2018, Leukemia, 33(2):531-536.
Aimo et al., "Therapies for cardiac light chain amyloidosis: An update" Int J Cardiology, Sep. 13, 2018, 271:152-160.
Bav et al.,"NT-proBNP: a new diagnostic screening tool to differentiate between patients with normal and reduced left ventricular systolic function," Heart, 2003, 89:2:150-154.
CAS Registry No. 945721-28-8, "Daratumumab," National Library of Medicine: ChemIDplus, retrieved on Jul. 26, 2022, retrieved from URL<https://chem.nlm.nih.gov/chemidplus/m/945721-28-8#:~:text=Substance%20Name%3A%20Daratumumab%20%5BUSAN%3A,RN%3A%20945721%2D28%2D8>, 2 pages.
Gertz et al., "Birtamimab in Patients with Mayo Stage IV AL Amyloidosis: Rationale for Confirmatory AFFIRM-AL Phase 3 Study." Poster P040. XVIII International Symposium on Amyloidosis, Sep. 4-8, 2022, Heidelberg, Germany.
Gertz et al., "Results of the Phase 3 VITAL Study of NEOD001 (Birtamimab) Plus Standard of Care in Patients with Light Chain (AL) Amyloidosis Suggest Survival Benefit for Mayo Stage IV Patients," Poster 3166, 61st American Society of Hematology Annual Meeting & Exposition, Dec. 7-10, 2019, Orlando, Florida.
Godara, "Combined use of two monoclonal antibodies in patients with systemic AL amyloidosis and cardiac involvement" Journal of Clinical Oncology, Meeting Abstract ASCO, 2019, 37(15):1.
Hester et al., "Diagnostic delay and characterization of the clinical prodrome in AL amyloidosis among 1523 US adults diagnosed between 2001 and 2019," Eur J Haematol. 107:428-435, 2021.
International Preliminary Report on Patentability in Appln. No. PCT/IB2020/000186, dated Aug. 25, 2021, 9 pages.
International Preliminary Report on Patentability in Appln. No. PCT/US2019/066648, dated Aug. 10, 2021, 9 pages.
International Search Report and Written Opinion in Appln. No. PCT/US2019/066648, dated Apr. 22, 2020, 14 pages.
Kumar et al., "Revised Prognostic Staging System for Light Chain Amyloidosis Incorporating Cardiac Biomarkers and Serum Free Light Chain Measurements," Joural of Clinical Oncology. Mar. 20. 2012, 30:989-995.
Lachmann et al., "Bispecific antibody: a tool for diagnosis and treatment of disease," Clin. Exp. Immunol., Mar. 1990,79:315-321.
Plieth, "Non-genetic amyloidosis lives again, thanks to Darzalex and Astra," Sep. 2021, Evaluate Vantage website, retrieved on May 23, 2022 from URL<https://www.evaluate.com/vantage/articles/news/deals/non-genetic-amyloidosis-lives-again-thanks-darzalex-and-astra>, 9 pages.
Plieth, "Takeda casts doubt on the remaining approach to amyloidosis," Jun. 6, 2019, Evaluate Vantage website, retrieved on May 23, 2022 from URL<https://www..evaluate.com/vantage/articles/analysis/takeda-casts-doubt-remaining-approach-amyloidosis>, 9 pages.
Pulido et al., "The six-minute walk test in patients with AL amyloidosis: a single centre case series", British Journal of Haematology, 2017, 177: 388-394.
Van De Donk et al., "CD 38 Anitbodies in Multiple Myeloma: Mechanisms of Action and Modes of Resistance" Frontiers in Immunology, Sep. 20, 2018, 9:1-12.
White et al., "Psychometric validation of the SF-36 Health Survey in light chain amyloidosis: results from community-based and clinic-based samples", Patient Related Outcome Measures, 2017, 8: 157-167.

SEQUENCE LISTING

<160> NUMBER OF SEQ ID NOS: 23

<210> SEQ ID NO 1
<211> LENGTH: 112
<212> TYPE: PRT
<213> ORGANISM: Artificial Sequence
<220> FEATURE:
<223> OTHER INFORMATION: Synthetic peptide

<400> SEQUENCE: 1

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Thr Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Phe Thr Phe Gly Gly Gly Thr Lys Val Glu Ile Lys
            100                 105                 110

<210> SEQ ID NO 2

```
<211> LENGTH: 119
<212> TYPE: PRT
<213> ORGANISM: Artificial Sequence
<220> FEATURE:
<223> OTHER INFORMATION: Synthetic peptide

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Tyr Trp Ile Arg Gln Ala Pro Gly Lys Gly Leu Glu Trp Val
        35                  40                  45

Ala Arg Ile Arg Ser Lys Ser Asn Asn Tyr Ala Ile Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Pro Tyr Ser Asp Ser Phe Ala Tyr Trp Gly Gln Gly
            100                 105                 110

Thr Leu Val Thr Val Ser Ser
        115

<210> SEQ ID NO 3
<211> LENGTH: 16
<212> TYPE: PRT
<213> ORGANISM: Artificial Sequence
<220> FEATURE:
<223> OTHER INFORMATION: Synthetic peptide

<400> SEQUENCE: 3

Arg Ser Ser Gln Ser Leu Val His Ser Thr Gly Asn Thr Tyr Leu His
1               5                   10                  15

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Lys Val Ser Asn Arg Phe Ser
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Ser Gln Ser Thr His Val Pro Phe Thr
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide
```

```
<400> SEQUENCE: 6

Gly Phe Thr Phe Asn Thr Tyr Ala Met Tyr
1               5                   10

<210> SEQ ID NO 7
<211> LENGTH: 19
<212> TYPE: PRT
<213> ORGANISM: Artificial Sequence
<220> FEATURE:
<223> OTHER INFORMATION: Synthetic peptide

<400> SEQUENCE: 7

Arg Ile Arg Ser Lys Ser Asn Asn Tyr Ala Ile Tyr Tyr Ala Asp Ser
1               5                   10                  15

Val Lys Asp

<210> SEQ ID NO 8
<211> LENGTH: 8
<212> TYPE: PRT
<213> ORGANISM: Artificial Sequence
<220> FEATURE:
<223> OTHER INFORMATION: Synthetic peptide

<400> SEQUENCE: 8

Pro Tyr Ser Asp Ser Phe Ala Tyr
1               5

<210> SEQ ID NO 9
<211> LENGTH: 16
<212> TYPE: PRT
<213> ORGANISM: Artificial Sequence
<220> FEATURE:
<223> OTHER INFORMATION: Synthetic peptide

<400> SEQUENCE: 9

Arg Ser Ser Leu Ser Leu Val His Ser Thr Gly Asn Thr Tyr Leu His
1               5                   10                  15

<210> SEQ ID NO 10
<211> LENGTH: 219
<212> TYPE: PRT
<213> ORGANISM: Artificial Sequence
<220> FEATURE:
<223> OTHER INFORMATION: Synthetic peptide

<400> SEQUENCE: 10

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Thr Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Phe Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125
```

```
Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 11
<211> LENGTH: 449
<212> TYPE: PRT
<213> ORGANISM: Artificial Sequence
<220> FEATURE:
<223> OTHER INFORMATION: Synthetic peptide

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Tyr Trp Ile Arg Gln Ala Pro Gly Lys Gly Leu Glu Trp Val
        35                  40                  45

Ala Arg Ile Arg Ser Lys Ser Asn Asn Tyr Ala Ile Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Pro Tyr Ser Asp Ser Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 12
<211> LENGTH: 449
<212> TYPE: PRT
<213> ORGANISM: Artificial Sequence
<220> FEATURE:
<223> OTHER INFORMATION: Synthetic peptide

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Tyr Trp Ile Arg Gln Ala Pro Gly Lys Gly Leu Glu Trp Val
        35                  40                  45

Ala Arg Ile Arg Ser Lys Ser Asn Asn Tyr Ala Ile Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Pro Tyr Ser Asp Ser Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 13
<211> LENGTH: 445
<212> TYPE: PRT
<213> ORGANISM: Artificial Sequence
<220> FEATURE:
<223> OTHER INFORMATION: Synthetic peptide

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Tyr Trp Ile Arg Gln Ala Pro Gly Lys Gly Leu Glu Trp Val
        35                  40                  45

Ala Arg Ile Arg Ser Lys Ser Asn Asn Tyr Ala Ile Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr

```
            85                  90                  95
Tyr Cys Ala Arg Pro Tyr Ser Asp Ser Phe Ala Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Asn Phe Gly Thr Gln Thr Tyr Thr Cys Asn Val Asp His Lys Pro
                195                 200                 205

Ser Asn Thr Lys Val Asp Lys Thr Val Glu Arg Lys Cys Cys Val Glu
            210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
                260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
            290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
            435                 440                 445

<210> SEQ ID NO 14
<211> LENGTH: 112
<212> TYPE: PRT
<213> ORGANISM: Artificial Sequence
<220> FEATURE:
<223> OTHER INFORMATION: Synthetic peptide

<400> SEQUENCE: 14

Asp Val Val Met Thr Gln Thr Pro Leu Ser Leu Pro Val Ser Leu Gly
```

```
                1               5                  10                  15
Asp Gln Ala Ser Ile Ser Cys Arg Ser Ser Gln Ser Leu Val His Arg
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Phe Cys Phe Gln Thr
                    85                  90                  95

Thr Tyr Val Pro Asn Thr Phe Gly Gly Gly Thr Lys Leu Glu Ile Lys
                100                 105                 110
```

<210> SEQ ID NO 15
<211> LENGTH: 111
<212> TYPE: PRT
<213> ORGANISM: Artificial Sequence
<220> FEATURE:
<223> OTHER INFORMATION: Synthetic peptide

<400> SEQUENCE: 15

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Ser Tyr
                20                  25                  30

Gly Val Ser Trp Val Arg Gln Pro Pro Gly Lys Gly Leu Glu Trp Leu
            35                  40                  45

Gly Val Ile Trp Gly Asp Gly Ser Thr Asn Tyr Lys Pro Asn Leu Met
        50                  55                  60

Ser Arg Leu Ser Ile Ser Lys Asp Ile Ser Lys Ser Gln Val Leu Phe
65                  70                  75                  80

Lys Leu Asn Ser Leu Gln Thr Asp Asp Thr Ala Thr Tyr Tyr Cys Val
                85                  90                  95

Thr Leu Asp Tyr Trp Gly Gln Gly Thr Ser Val Thr Val Ser Ser
                100                 105                 110
```

<210> SEQ ID NO 16
<211> LENGTH: 16
<212> TYPE: PRT
<213> ORGANISM: Artificial Sequence
<220> FEATURE:
<223> OTHER INFORMATION: Synthetic peptide

<400> SEQUENCE: 16

```
Arg Ser Ser Gln Ser Leu Val His Arg Asn Gly Asn Tyr Thr Leu His
1               5                   10                  15
```

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide

<400> SEQUENCE: 17

```
Leu Val Ser Asn Arg Phe Ser
1               5
```

<210> SEQ ID NO 18

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 18

Phe Asn Thr Thr Tyr Val Pro Asn Thr
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic peptide

<400> SEQUENCE: 19

Ser Tyr Gly Val Ser Trp
1               5

<210> SEQ ID NO 20
<211> LENGTH: 21
<212> TYPE: PRT
<213> ORGANISM: Artificial Sequence
<220> FEATURE:
<223> OTHER INFORMATION: Synthetic peptide

<400> SEQUENCE: 20

Val Ile Trp Gly Asp Gly Ser Thr Asn Tyr His Pro Asn Leu Met Ser
1               5                   10                  15

Arg Leu Ser Ile Ser
            20

<210> SEQ ID NO 21
<211> LENGTH: 3
<212> TYPE: PRT
<213> ORGANISM: Artificial Sequence
<220> FEATURE:
<223> OTHER INFORMATION: Synthetic peptide

<400> SEQUENCE: 21

Leu Asp Tyr
1

<210> SEQ ID NO 22
<211> LENGTH: 336
<212> TYPE: DNA
<213> ORGANISM: Artificial Sequence
<220> FEATURE:
<223> OTHER INFORMATION: 11-1F4 monoclonal antibody variable light

<400> SEQUENCE: 22
gatgttgtga tgacccaaac tccactctcc ctgcctgtca gtcttggaga tcaagcctcc    60
atctcttgca gatctagtca gagccttgta catagaaatg gaaacaccta tttacattgg   120
tacctgcaga agccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tttgggactt tatttctgtt ttcaaactac atatgttccg   300
aacacgttcg gagggggac caagctggaa ataaaa                              336

<210> SEQ ID NO 23
<211> LENGTH: 333
<212> TYPE: DNA
```

```
<213> ORGANISM: Artificial Sequence
<220> FEATURE:
<223> OTHER INFORMATION: 11-1F4 monoclonal antibody variable heavy

<400> SEQUENCE: 23
caggtgcagc tgaaggagtc aggacctggc ctggtggcgc cctcacagag cctgtccatc      60
acatgcactg tctcagggtt ctcattaagc agctatggtg taagctgggt tcgccagcct     120
ccaggaaagg gtctggagtg gctgggagta atatgggtg acgggagcac aaattatcat      180
ccaaatctca tgtccagact gagtatcagc aaggatattt ccaagagcca agttctcttc    240
aaactgaata gtctgcaaac tgatgacaca gccacgtact actgtgtcac cttcgactac    300
tggggtcaag gaacctcagt caccgtctcc tca                                  333
```

METHODS OF TREATING AL AMYLOIDOSIS

RELATED APPLICATIONS

The application claims the benefit of U.S. Provisional Patent Application Ser. No. 62/814,252, filed Mar. 5, 2019 and U.S. Provisional Patent Application Ser. No. 62/942,722, filed Dec. 2, 2019, each of which is incorporated by reference herein in its entirety.

FIELD

The disclosure relates to the technical fields of immunology and medicine.

REFERENCE TO SEQUENCE LISTING

This application contains a Sequence Listing submitted as an electronic text file named "19-467-US_Sequence-Listing_ST25.txt", having a size in bytes of 22 kb, and created on Mar. 5, 2020. The information contained in this electronic file is hereby incorporated by reference in its entirety pursuant to 37 CFR § 1.52(e)(5).

BACKGROUND

AL amyloidosis involves a hematological disorder caused by clonal plasma cells that produce immunoglobulin light chains that can misfold and contribute to disease. Overproduction of misfolded light chain by plasma cells results in deposits of abnormal AL protein (amyloid) in the tissues and organs of individuals with AL amyloidosis. Clinical features of AL amyloidosis include a constellation of symptoms and organ dysfunction that can include cardiac, renal, and hepatic dysfunction, gastrointestinal involvement, neuropathies and macroglossia. The mechanisms by which amyloidogenic immunoglobulin light chains result in organ dysfunction are not well characterized, however, it is hypothesized that both amyloid deposits and prefibrillar aggregates may contribute to cytotoxic effects on organs observed in patients with AL amyloidosis. AL amyloidosis is a disease entity of its own, although AL amyloidosis can occur concurrently in a subset of patients with multiple myeloma (up to 15%) or monoclonal gammopathy of unknown significance (MGUS; up to 9%).

AL amyloidosis is a rare disorder with an estimated incidence of 8 in 1,000,000 people. Only 1200 to 3200 new cases of AL amyloidosis are reported each year in the United States. Two thirds of patients with AL amyloidosis are male and less than 5% of patients are under 40 years of age. Both the causes and origins of AL amyloidosis remain poorly understood. The outcome of the disease for patients with AL amyloidosis can be predicted based on the Mayo four stage prognostic staging system discussed in Kumar et al., 2012 (Kumar et al., Revised Prognostic Staging System for Light Chain Amyloidosis Incorporating Cardiac Biomarkers and Serum Free Light Chain Measurements, J Clin Oncol 30:989-995 2012), with the outcome for Stage IV patients being quite dire.

Current treatment of patients with AL amyloidosis is aimed at reducing or eliminating the bone marrow disorder, i.e. the plasma cells that are responsible for producing the light chains, thereby limiting or halting the production of amyloid. The most aggressive treatment options include stem cell transplant and high-dose chemotherapy for those patients who can tolerate it. Other treatment regimens include combinations of drugs often used to treat hematological malignancies, such as melphalan, prednisone, dexamethasone and proteosome inhibitors such as bortezomib, in an attempt to reduce light chain production. There are no currently approved treatments for AL amyloidosis, and none that directly target potentially toxic forms of the amyloidogenic proteins. While some treatment options may ameliorate some of the morbidity associated with AL amyloidosis, few if any have been demonstrated to improve the prognosis in patients. Furthermore, Mayo Stage IV patients with AL amyloidosis represent a patient subset with a very high burden of morbidity and mortality, with no currently approved treatments, and population estimates of approximately 2,760 patients in the U.S., and from 6,900 to 10,350 patients in the U.S. and the European Union combined.

Thus, there is an unmet need for therapies that improve health status, including reducing the risk of mortality or enhancing the quality of life in patients with AL amyloidosis.

SUMMARY

The present disclosure relates to methods of treating certain AL amyloidosis patients.

Provided herein are methods of treating a patient having AL amyloidosis, comprising determining the Mayo Stage of the patient's AL amyloidosis, and/or the 6 minute walk distance (6MWD) and ejection fraction (EF) of the patient, or determining the Mayo Stage and EF of the patient, selecting the patient for treatment with an antibody which competes for binding to human amyloid A peptide or human kappa or lambda light chain immunoglobulin with 2A4 (ATCC Accession Number PTA-9662) or 7D8 (ATCC Accession Number PTA-9468), or competes for binding to human kappa (κ) or lambda light chain immunoglobulin with 11-1F4 (ATCC Accession Number PTA-105) if the patient has Mayo Stage IV AL amyloidosis, has a 6MWD≥150 meters and an EF>50% at baseline, has Mayo Stage IV and EF>50% at baseline, or has Mayo Stage IV, a 6MWD≥150 meters and an EF>50% at baseline, and administering an effective dosage of the antibody. In some embodiments, the patient has Mayo Stage IV AL amyloidosis. Some such Mayo Stage IV patients have an EF>50%, and some of such patients also have a 6MWD≥150 meters.

Also provided herein are methods of treating a patient having AL amyloidosis, comprising administering an effective dosage of an antibody which competes for binding to human amyloid A peptide or human kappa or lambda light chain immunoglobulin with 2A4 (ATCC Accession Number PTA-9662) or 7D8 (ATCC Accession Number PTA-9468), or competes for binding to κ or lambda light chain immunoglobulin with 11-1F4 (ATCC Accession Number PTA-105), wherein the patient has (a) Mayo Stage IV AL amyloidosis (b) a 6 minute walk distance (MWD) 150 meters and an ejection fraction (EF)>50%, (c) Mayo Stage IVC and an EF>50% or (d) Mayo Stage IV and a 6MWD≥150 meters and an EF>50%. In some embodiments, the patient has Mayo Stage IV AL amyloidosis. In some embodiments, the patient has a 6MWD≥150 meters and an EF>50%, and some of such patients have Mayo Stage IV AL amyloidosis. In some embodiments, the Mayo Stage IV patients have an EF>50%.

Provided herein are methods of treating a Mayo Stage IV patient with AL amyloidosis comprising administering an effective dosage of an antibody which competes for binding to human amyloid A peptide or human kappa or lambda light chain immunoglobulin with 2A4 (ATCC Accession Number PTA-9662) or 7D8 (ATCC Accession Number PTA-9468), or competes for binding to human kappa (κ) or lambda light chain immunoglobulin with 11-1F4 (ATCC Accession Number PTA-105). In some embodiments, the method reduces the risk of mortality in the patient. In some embodiments, the method reduces the risk of all-cause mortality in the patient. In some embodiments, the method of treatment reduces the risk of cardiac mortality in the patient.

Provided herein are methods of treating a Mayo Stage IV patient with AL amyloidosis comprising administering an effective dosage of birtamimab. In some embodiments, the method reduces the risk of mortality in the patient. In some embodiments, the method reduces the risk of all-cause mortality in the patient. In some embodiments, the method of treatment reduces the risk of cardiac mortality in the patient. In some embodiments, the dosage is from about 0.5 mg/kg to about 30 mg/kg, and birtamimab is administered intravenously or subcutaneously at a frequency of from about weekly to about quarterly. In some embodiments, the dosage is about 24 mg/kg and birtamimab is administered intravenously every 28 days.

In some embodiments provided herein, antibody comprises a light chain variable region comprising three complementarity determining regions of 2A4, 7D8 or 11-1F4, and a heavy chain variable region comprising three complementarity determining regions of 2A4, 7D8 or 11-1F4, respectively. In some embodiments, the antibody is a humanized version of 2A4. In some embodiments the antibody is a humanized or chimeric version of 11-1F4.

In some embodiments, the antibody binds to the same epitope as 2A4, 7D8 or 11-1F4. In some embodiments the patient is administered an antibody which competes for binding to human amyloid A peptide or human kappa or lambda light chain immunoglobulin with 2A4 (ATCC Accession Number 9662) or or competes for binding to κ or lambda light chain immunoglobulin with 11-1F4 (ATCC Accession Number PTA-105). In some embodiments, the antibody binds to the same epitope as 2A4 or 11-1F4. In some embodiments, the antibody is a humanized version of 2A4. In some embodiments, the antibody is a humanized or chimeric version of 11-1F4. In some embodiments, the antibody is a humanized bispecific or multispecific version containing combinations of 11-1F4, 2A4, and/or 7D8.

In some embodiments provided herein, the antibody comprises a light chain variable region comprising three complementarity determining regions set forth as SEQ ID NOs: 3, 4 and 5, or SEQ ID NOs: 16, 17, and 18, and a heavy chain variable region comprising three complementarity determining regions set forth as SEQ ID NOs: 6, 7 and 8, or SEQ ID NOs:19, 20, and 21. In some embodiments, the light chain variable region of the antibody comprises the amino acid sequence set forth as SEQ ID NO: 1 or 14. In some embodiments, the heavy chain variable region of the antibody comprises the amino acid sequence set forth as SEQ ID NO: 2 or 15. In some embodiments, the light chain variable region comprises the amino acid sequence set forth as SEQ ID NO: 1 or 14 and the heavy chain variable region comprises the amino acid sequence set forth as SEQ ID NO: 2 or 15. In some embodiments provided herein, the antibody comprises a light chain comprising the amino acid sequence set forth as SEQ ID NO:10 and a heavy chain comprising the amino acid sequence set forth as SEQ ID NO: 11, 12 or 13. In some embodiments, the antibody comprises a light chain comprising the amino acid sequence set forth as SEQ ID NO:10 and a heavy chain comprising the amino acid sequence set forth as SEQ ID NO:12. In some embodiments, the antibody is birtamimab.

In some embodiments provided herein, the patient is newly diagnosed and AL amyloidosis treatment naïve. In some embodiments, the patient previously received or concomitantly receives treatment with melphalan, prednisone, dexamethasone, bortezomib, cyclophosphamide, lenalidomide, doxorubicin, doxycycline, daratumumab, autologous transplant or a combination thereof. In certain methods, the patient previously received or concomitantly receives treatment with humanized 2A4, 7D8, or 11-1F4 in advance of receiving plasma cell therapy.

Provided herein are methods comprising administering to a Mayo Stage IV patient an effective dosage of an antibody which competes for binding to human amyloid A peptide or human kappa or lambda light chain immunoglobulin with antibody 2A4 (ATCC Accession Number 9662) or 7D8 (ATCC Accession Number PTA-9468), or competes for binding to kappa light chain immunoglobulin with 11-1F4 (ATCC Accession Number PTA-105), thereby reducing the patient's relative risk of mortality by at least about 35%.

Also provided herein are methods of treating a patient with AL amyloidosis, comprising determining that the patient has a 6 minute walk distance (6MWD)≥150 meters and an ejection fraction (EF)>50%, selecting the patient for treatment with an antibody which competes for binding to human amyloid A peptide or human kappa or lambda light chain immunoglobulin with antibody 2A4 (ATCC Accession Number PTA-9662) or 7D8 (ATCC Accession Number PTA-9468), or competes for binding to kappa light chain immunoglobulin with 11-1F4 (ATCC Accession Number PTA-105), and administering an effective dosage of the antibody.

Also provided herein are methods of treating a patient with AL amyloidosis who has a demonstrated 6 minute walk distance (6MWD) of greater than or equal to 150 meters and an ejection fraction (EF) of more than 50%, comprising administering to the patient an effective dosage of an antibody which competes for binding to human amyloid A peptide or human kappa or lambda light chain immunoglobulin with antibody 2A4 (ATCC Accession Number PTA-9662) or 7D8 (ATCC Accession Number PTA-9468), or competes for binding to κ light chain immunoglobulin with 11-1F4 (ATCC Accession Number PTA-105).

Also provided herein are methods of improving a 6 minute walk distance (6MWD) in a patient having AL amyloidosis, comprising administering to the patient an effective dosage of an antibody which competes for binding to human amyloid A peptide or human kappa or lambda light chain immunoglobulin with antibody 2A4 (ATCC Accession Number PTA-9662) or 7D8 (ATCC Accession Number PTA-9468), or competes for binding to kappa light chain immunoglobulin with 11-1F4 (ATCC Accession Number PTA-105). In some embodiments, the patient has Mayo Stage IV AL amyloidosis. In some embodiments, the patient has an EF>50%. In some embodiments, the Mayo Stage IV patients have an EF>50%.

Also provided herein are methods of reducing the risk of mortality in a patient with AL amyloidosis by at least 45% relative to control conditions (relative risk), comprising administering to the patient an effective dosage of an antibody which competes for binding to human amyloid A peptide or human kappa or lambda light chain immunoglobulin with antibody 2A4 (ATCC Accession Number PTA-9662) or 7D8 (ATCC Accession Number PTA-9468), or competes for binding to kappa light chain immunoglobulin with 11-1F4 (ATCC Accession Number PTA-105), wherein the patient has Mayo Stage IV AL amyloidosis and/or has a demonstrated 6 minute walk distance (6MWD)

of greater than or equal to 150 meters and an ejection fraction (EF) of more than 50% or has Mayo Stage IV AL amyloidosis and an EF>50%. In some embodiments, the method reduces the risk of all-cause mortality in the patient. In some embodiments, the risk of all-cause mortality is reduced by at least about 48.9% relative to control conditions. In some embodiments, the risk of all-cause mortality is reduced by at least about 50% relative to control conditions. In some embodiments, the risk of all-cause mortality is reduced by at least about 50.2% relative to control conditions. In some embodiments, the risk of all-cause mortality is reduced by at least about 60% relative to control conditions. In some embodiments, the risk of all-cause mortality is reduced by at least about 70% relative to control conditions. In some embodiments the risk of all-cause mortality is reduced by at least about 75% relative to control conditions. In some embodiments, the risk of all-cause mortality is reduced by at least about 79.9% relative to control conditions. In some embodiments, the risk of all-cause mortality is reduced by at least 81.5% relative to control conditions. In some embodiments, the method reduces the risk of cardiac mortality in the patient. In some embodiments, the risk of cardiac mortality is reduced by at least about 62.2% relative to control conditions. In some embodiments, the risk of cardiac mortality is reduced by at least about 75% relative to control conditions.

In some embodiments provided herein, the patient exhibits improvement in the 36-Item Short Form Survey Physical Component Score (SF-36 PCS) or SF-36v2 following treatment with the antibody. In some embodiments, after nine months of treatment the change in the patient's score on the SF-36 PCS or SF-36v2 is at least 5 points higher relative to a different patient at the same time point who has not been administered the antibody.

In some embodiments provided herein, the effective dosage of the antibody is administered from a pharmaceutical formulation comprising the antibody at a concentration within the range from about 1 mg/mL to about 100 mg/mL. In some embodiments provided herein, the effective dosage of the antibody is administered from a pharmaceutical formulation comprising, histidine buffer at a concentration within the range from about 20 mM to about 30 mM, trehalose at a concentration within the range from about 210 mM to about 250 mM, and polysorbate 20 at a concentration within the range from about 0.005% to about 0.05% by weight, and the formulation has a pH within the range from about 6 to about 7. In some embodiments, the dosage is from about 0.5 mg/kg to about 30 mg/kg and the antibody is administered intravenously or subcutaneously at a frequency of from about weekly to about quarterly. In some embodiments, the antibody is present at a concentration of about 50 mg/mL. In some embodiments provided herein, the pharmaceutical formulation comprises, the histidine buffer at a concentration of about 25 mM, the trehalose at a concentration of about 230 mM, the polysorbate 20 at a concentration of about 0.2 g/L, and the pH is about 6.5.

In some embodiments provided herein, the dosage is administered subcutaneously without dilution from a vial containing the formulation. In some embodiments, the dosage is administered intravenously following the transfer of an amount of the formulation required for the dosage from a vial to an intravenous bag containing a liquid.

In some embodiments provided herein, the dosage is about 24 mg/kg and the antibody is administered intravenously every 28 days. In some embodiments provided herein, the dosage is administered intravenously (IV) at 24 mg/kg (dose not to exceed 2500 mg) once every 28 days (±5 days). In some embodiments, the duration of the treatment is at least 9 months. In some embodiments, the duration of the treatment is at least 12 months. In some embodiments, the duration is effective to achieve or maintain at least about a 3 point increase from baseline in SF-36 PCS.

In some embodiments provided herein, the antibody is a Fab, Fab', F(ab')$_2$, F(ab)c, Dab, nanobody or Fv.

Also provided herein is an antibody which competes for binding to human amyloid A peptide or human kappa or lambda light chain immunoglobulin with antibody 2A4 (ATCC Accession Number PTA-9662) or 7D8 (ATCC Accession Number PTA-9468), or competes for binding to kappa light chain immunoglobulin with 11-1F4 (ATCC Accession Number PTA-105) for use in a method of treating a patient with Mayo Stage IV AL amyloidosis, a patient who has at baseline a demonstrated 6 minute walk distance (6MWD) of greater than or equal to 150 meters and an ejection fraction (EF) of more than 50%, a Mayo Stage IV patient who has at baseline an EF of more than 50%, or a Mayo Stage IV patient who has at baseline a 6MWD of greater than or equal to 150 meters and an EF of more than 50%. In some embodiments, the antibody is a humanized version of 2A4. Some such antibodies comprise a light chain variable region comprising three complementarity determining regions set forth as SEQ ID NOs: 3, 4 and 5, or SEQ ID NO:16, 17, and 18, and a heavy chain variable region comprising three complementarity determining regions set forth as SEQ ID NOs: 6, 7 and 8, or SEQ ID NOs:19, 20 and 21. In some antibodies the light chain variable region comprises the amino acid sequence set forth as SEQ ID NO: 1 of 14. In some antibodies, the heavy chain variable region comprises the amino acid sequence set forth as SEQ ID NO: 2 or 15. In some antibodies the light chain variable region comprises the amino acid sequence set forth as SEQ ID NO: 1 or 14 and the heavy chain variable region comprises the amino acid sequence set forth as SEQ ID NO: 2 or 15.

Some antibodies provided herein are formulated as a pharmaceutical formulation comprising the antibody at a concentration within the range from about 1mg/mL to about 100 mg/mL, histidine buffer at a concentration within the range from about 20 mM to about 30 mM, trehalose at a concentration within the range from about 210 mM to about 250 mM, polysorbate 20 at a concentration within the range from about 0.005% to about 0.05% by weight, and the pharmaceutical formulation is characterized by a pH within the range from about 6 to about 7.

Some uses of the antibody comprise a dosage from about 0.5 mg/kg to about 30 mg/kg and wherein the antibody is administered intravenously or subcutaneously at a frequency of from about weekly to about quarterly. For some uses, the antibody is present at a concentration of about 50 mg/mL, the histidine buffer is present at a concentration of about 25 mM, the trehalose is present at a concentration of about 230 mM, the polysorbate 20 is present at a concentration of about 0.2 g/L, and the pH is about 6.5.

Also provided herein are methods of identifying a patient likely to receive a health benefit from treatment with an antibody which competes for binding to human amyloid A peptide or human kappa or lambda light chain immunoglobulin with antibody 2A4 (ATCC Accession Number PTA-9662) or 7D8 (ATCC Accession Number PTA-9468), or competes for binding to kappa light chain immunoglobulin with 11-1F4 (ATCC Accession Number PTA-105), comprising determining (a) whether the patient has Mayo Stage I, Stage II, Stage III or Stage IV AL amyloidosis, (b) the 6 minute walk distance (6MWD) of the patient, and/or (c) the ejection fraction (EF) of the patient, and selecting for treatment a patient with (i) Stage IV AL amyloidosis, (ii) a patient with a 6MWD≥150 meters and an EF>50%, (iii) Stage IV AL amyloidosis and a 6MWD≥150 meters and an EF>50%, or (iv) Stage IV AL amyloidosis and an EF>50%. In some embodiments, the selected patient has Mayo Stage IV AL amyloidosis. In some embodiments, the selected patient has a 6MWD≥150 meters and an ejection fraction>50%. In some embodiments, the selected patient has Mayo Stage IV AL amyloidosis and a 6MWD≥150 meters and an ejection fraction>50%. Some methods further comprise administering intravenously to the patient a dose in the range of about 0.5 mg/m2 to about 500 mg/m2 of a chimeric or humanized version of 11-1F4, or a dose in the range of about 0.5 mg/kg to about 30 mg/kg of a humanized version of 2A4.

DESCRIPTION

Figure 1A:
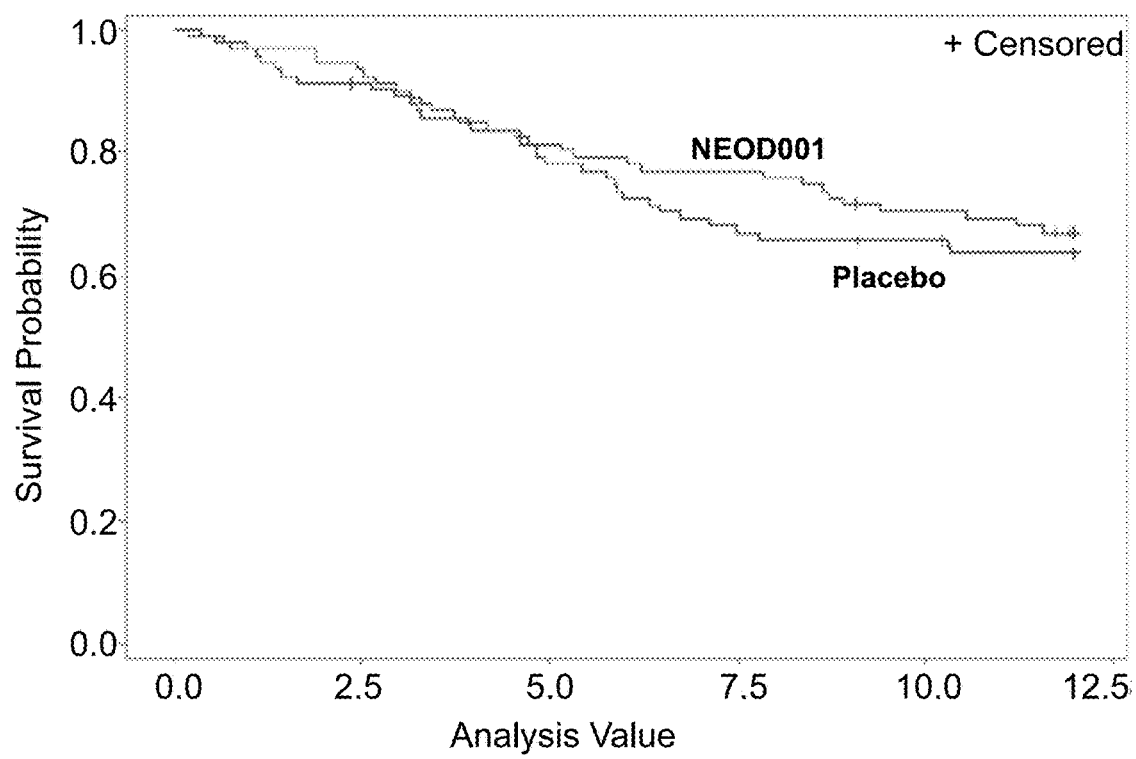
FIGS. 1A-1B show the primary endpoint through 12 months (all-cause mortality or cardiac hospitalization 91 days) in AL amyloidosis patients treated with NEOD001 vs placebo in Mayo Stage I-III patients (FIG. 1A) and Mayo Stage IV patients (FIG. 1B), respectively.

The disclosure provides methods of treating certain AL amyloidosis patients, namely patients with Mayo Stage IV AL amyloidosis, patients with a baseline six minute walk distance (6MWD; sometimes refered to as the six minute walk test (6MWT) distance) greater than or equal to 150 meters and ejection fraction (EF) greater than 50%, Mayo Stage IV patients with a baseline EF greater than 50%, and Mayo Stage IV patients with a baseline 6MWD greater than or equal to 150 meters and ejection fraction (EF) greater than 50%. The methods involve administering to such patients an antibody which competes for binding to human amyloid A peptide or human kappa or lambda light chain immunoglobulin with antibody 2A4 (ATCC Accession Number PTA-9662) or antibody 7D8 (ATCC Accession Number PTA-9468) or which competes for binding to kappa immunoglobulin light chain with antibody 11-1F4 (ATCC Accession Number PTA-150). In some embodiments, the antibody is birtamimab.

1. Definitions

The term "antibody" includes intact antibodies and antigen-binding fragments thereof. Typically, fragments compete with the intact antibody from which they were derived for specific binding to the target including separate heavy chains, light chains Fab, Fab', F(ab')$_2$, F(ab)c, Dabs, nanobodies, and Fv. Fragments can be produced by recombinant DNA techniques, or by enzymatic or chemical separation of intact immunoglobulins. The term "antibody" also includes a bispecific or multispecific antibody and/or a humanized antibody. A bispecific or bifunctional or multifunctional antibody is an artificial hybrid antibody having two or more different heavy/light chain pairs and two or more different binding sites (see, e.g., Songsivilai and Lachmann, *Clin. Exp. Immunol.*, 79:315-321 (1990); Kostelny et al., *J. Immunol.*, 148:1547-53 (1992)).

The term "censoring" refers to a situation in which the value of a measurement or observation is only partially known. For example, if a study is conducted to measure the impact of a drug on mortality rate, survival will be assumed for the period of the study in the absence of data indicating death, such that patients who withdrew from the study are considered to be alive through the duration of the study regardless of their unknown disposition (i.e., alive or dead).

The term "ejection fraction" or "EF" refers to the measurement of how much blood the left ventricle pumps out with each contraction. An ejection fraction of 50 percent means that 50 percent of the total amount of blood in the left ventricle is pushed out with each heartbeat. Ejection fraction is used as a measure of heart failure. The EF of a normal heart is typically between 50-70 percent. 41-49 percent may be considered borderline and an EF under 40 percent may be evidence of heart failure or cardiomyopathy.

The term "hazard ratio" or "HR" reflects the instantaneous probability (i.e., hazard rate) of an event (death or progression) in the experimental arm as a ratio to the probability in the comparator arm. If the HR is 1.0, there is no clear advantage for either arm. The lower the HR value, the greater the reduction in risk of death or progression for the experimental treatment arm of the study, which is calculated as 1-HR. For example, an HR of 0.84 equals a 16% relative reduction in event risk in comparison with the control arm of the study.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

The term "Mayo Stage IV patients" or "Stage IV" refers to patients with stage IV disease according to the prognostic staging system established by the Mayo Clinic (Kumar et al., Revised Prognostic Staging System for Light Chain Amyloidosis Incorporating Cardiac Biomarkers and Serum Free Light Chain Measurements, *J Clin Oncol* 30:989-995 2012), which incorporates both cardiac biomarkers and level of amyloidogenic light chain synthesis. Collectively, patients with stage I, stage II or stage III disease are referred to herein as "Mayo Stage I-III patients" or "Stage I-III patients". In some embodiments, a patient is identified as having Stage IV AL amyloidosis if they meet the criteria for the following three prognostic variables: troponin-T (cTnT)≥0.025 ng/mL, N-terminal pro-B-type natriuretic peptide (NT-ProBNP)≥1, 800 pg/mL, and difference between involved and univolved light chain (FLC-diff or dFLC)≥18 mg/dL). In certain embodiments, a patient can be confirmed as Mayo Stage IV as defined by: (1) NT-proBNP≥1800 pg/mL, (2) Troponin-T>0.03 ng/mL, and (3) dFLC≥18 mg/dL.

The term "p-value" or "p" refers to a number between 0 and 1 relating to the significance of results obtained. A small p-value indicates strong evidence against the null hypothesis (i.e., the hypothesis that there is no effect), for example ≤0.1, indicates statistical significance, with p≤0.001 being statistically highly significant (less than one in a thousand chance of being wrong).

The phrase "substantially from a human immunoglobulin or antibody" means that, when aligned to a human immunoglobulin or antibody amino sequence for comparison purposes, the region shares at least 80-90%, preferably 90-95%, more preferably 95-99% identity (i.e., local sequence identity) with the human framework or constant region sequence, allowing, for example, for conservative substitutions, consensus sequence substitutions, germline substitutions, backmutations, and the like. The introduction of conservative substitutions, consensus sequence substitutions, germline substitutions, backmutations, and the like, is often referred to as "optimization" of a humanized antibody or chain. The phrase "substantially from a non-human immunoglobulin or antibody" or "substantially non-human" means having an immunoglobulin or antibody sequence at least 80-95%, preferably 90-95%, more preferably, 96%, 97%, 98%, or 99% identical to that of a non-human organism, e.g., a non-human mammal.

Accordingly, all regions or residues of a humanized immunoglobulin or antibody, or of a humanized immunoglobulin or antibody chain, except possibly the CDRs, are substantially identical to the corresponding regions or residues of one or more native human immunoglobulin sequences. The term "corresponding region" or "corresponding residue" refers to a region or residue on a second amino acid or nucleotide sequence which occupies the same (i.e., equivalent) position as a region or residue on a first amino acid or nucleotide sequence, when the first and second sequences are optimally aligned for comparison purposes.

The phrases "risk reduction" and "risk of" refer to the relative risk unless specified to mean absolute risk.

II. Methods of Treatment and Amenable Subjects

Patients amenable to treatment can be identified by determining the Mayo Stage of the patient's AL amyloidosis. Alternatively, or in addition, patients likely to receive a health benefit from the treatment can be identified by determining the 6MWD of the patient and determining the ejection fraction of the patient. Patients likely to respond positively to treatment are those with Stage IV AL amyloidosis, patients with a 6MWD of ≥150 meters and an EF of >50% at baseline, patients with Mayo Stage IV AL amyloidosis with an EF of >50% at baseline, and Mayo Stage IV patients with a 6MWD of ≥150 meters and an EF of >50% at baseline.

Provided herein are methods of treating a human patient showing symptoms of or diagnosed with Mayo Stage IV AL amyloidosis and/or a human patient having a baseline 6MWD of p24 150 meters and a baseline EF of >50%, comprising administering to the patient a regimen of any of the antibodies or antibody formulations described herein effective to improve the health status of the patient. Some of the patients have Mayo Stage IV AL amyloidosis and a human patient having a baseline 6MWD of ≥150 meters and a baseline EF of >50%. Some patients have Mayo Stage IV AL amyloidosis and a baseline EF of >50%. Some patients have systemic organ dysfunction attributed to AL amyloidosis, including dysfunction of the heart, kidney, liver, peripheral nervous system, gastrointestinal system, autonomic nervous system, lung, and/or soft tissue or lymphatic system.

Some methods involve determining the baseline level of troponin-T, NT-proBNP and relative levels of involved and uninvolved light chain in a patient, selecting the patient for treatment if the patient has a baseline level of cTnT 0.025≥ng/mL or >0.03 ng/mL, NT-ProBNP 1,800≥pg/mL (and <8500 pg/mL) and FLC-diff≥18 mg/dL, and administering an effective dosage of any of the antibodies disclosed herein. Some methods involve determining the 6MWD and EF of a patient at baseline and selecting the patient for treatment if the patient has a 6MWD of ≥150 meters and an EF of >50%. In some instances, Mayo Stage IV patients with baseline 6MWD of ≥150 meters and baseline EF of >50% are selected for treatment. Some methods involve determining the Mayo Stage and EF of the patient and in some instances Mayo Stage IV patients with a baseline EF of >50% are selected for treatment.

In some embodiments, the patient is treatment naïve, meaning that the patient has not previously received any treatment for AL amyloidosis. Patients amenable to treatment also include those patients who have received, are currently receiving, or will later receive an alternate therapy for treatment of AL amyloidosis or an associated condition, such as, inflammatory diseases, chronic microbial infections, malignant neoplasms, inherited inflammatory diseases, and lymphoproliferative disorders. For example, patients may also receive or have received one or more of the therapeutic agents identified herein with respect to combination therapies. As an example, patients suffering from AL amyloidosis may also receive or have received or may later receive bortezomib, melphalan, lenalidomide, prednisone, dexamethasone, cyclophosphamide, pomalidomide, carfilzomib, doxorubicin, doxycycline, daratumumab, autologous transplant or combinations thereof. For those patients who have previously received alternate therapies for the treatment of amyloid disease, such therapies may or may not have been successful by the relevant clinical measures, and likely did not improve health status. Additional examples of such therapies include (1) CyBorD, which is a combination therapy comprising cyclophosphamide, bortezomib and dexamethasone, (2) BMDex, which is a combination of bortezomib, melphalan and dexamethasone, (3) MDex, which is a combination of melphalan and dexamethasone, (4) LDex, which is a combination of lenalidomide and dexamethasone, (5) CLD, which is a combination of cyclophosphamide, lenalidomide and dexamethasone, (6) PomDex, which is a combination of pomalidomide and dexamethasone, and (7) CRd, which is a combination of lenalidomide, cyclophosphamide and dexamethasone. Such patients may, or may not, have experienced cardiac and/or renal improvement as a result of such treatment.

An improvement in health status can be established when the patient exhibits an improvement in the six minute walk distance (meters) outcome measure (6MWD).

An improvement in the 36-Item Short Form Survey Physical Component Score (SF-36 PCS) or Short Form 36 questionnaire (SF-36v2) can also indicate an improvement in health status of the patient. For example, a patient treated with an antibody for at least nine months who scores at least 5 points higher on the SF-36 PCS or SF-36v2 questionnaire than a different patient at the same time point who has not received the antibody has achieved an improvement in health status. In some embodiments, treatment with an antibody disclosed herein results in an increase of a patient's PCS, as measured by SF-36 or SF36v2, of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, or at least 99. In some embodiments, treatment with an antibody disclosed herein results in an increase of a patient's PCS, as measured by SF-36 or SF36v2, of about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, or about 100.

Reduced length of hospitalization stays or reduced frequency of hospitalization for more than 90 days of patients treated with the antibodies disclosed herein compared to patients who have not received antibody can also indicate an improvement in health status of the patient. Improvement in health status can also be shown by longer survival of the antibody treated patient compared to untreated patients around the same time. In some embodiments, treatment with an antibody disclosed herein can reduce the risk of all-cause mortality for the treated patient by at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% relative to control treated patients, as can be determined by calculating hazard ratios between the treated patient and untreated patients.

In some embodiments, treatment with the antibodies disclosed herein can reduce the risk of all-cause mortality for the treated patient by about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% relative to control treated patients, as can be determined by calculating hazard ratios between the treated patient and untreated patients. In some embodiments, treatment with the antibodies disclosed herein can reduce the risk of all-cause mortality for the treated patient by about 45%, 48.9%, 50%, 50.2%, 60%, 62.2%, 65%, 70%, 75%, 79.9%, 80% or 81.5% relative to control treated patients, as can be determined by calculating hazard ratios between the treated patient and untreated patients.

For example, the risk of all-cause mortality for some Mayo Stage IV patients can be reduced by about 50.2%, and by about 79.9% for some Mayo Stage IV patients if such patients have some level of functional reserve prior to treatment as defined by baseline 6MWD of ≥150 meters and an ejection fraction of >50%.

In some embodiments, the risk of all-cause mortality for some Mayo Stage IV patients can be reduced by at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% if they have an ejection fraction of >50%. In some embodiments, the risk of all-cause mortality for some Mayo Stage IV patients can be reduced by about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% if they have an ejection fraction of >50%. In some embodiments, the risk of all-cause mortality for some Mayo Stage IV patients can be reduced by about 81.5% if they have an ejection fraction of >50%.

In some embodiments, the risk of all-cause mortality some patients having a baseline 6MWD of ≥150 meters and an ejection fraction of >50%, regardless of Mayo Stage, can be reduced by at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% if they have an ejection fraction of >50%. In some embodiments, the risk of all-cause mortality some patients having a baseline 6MWD of ≥150 meters and an ejection fraction of >50%, regardless of Mayo Stage, can be reduced by about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% if they have an ejection fraction of >50%. In some embodiments, the risk of all-cause mortality in some patients having a baseline 6MWD of ≥150 meters and an ejection fraction of >50%, regardless of Mayo Stage, can be reduced by about 48.9%. The risk of cardiac mortality for some Mayo Stage IV patients can be reduced by about 62.2%.

In some embodiments, treatment with an antibody disclosed herein results in an increase of a patient's 6MWD by at least 1 meter, at least 2 meters, at least 3 meters, at least 4 meters, at least 5 meters, at least 6 meters, at least 7 meters, at least 8 meters, at least 9 meters, at least 10 meters, at least 11 meters, at least 12 meters, at least 13 meters, at least 14 meters, at least 15 meters, at least 16 meters, at least 17 meters, at least 18 meters, at least 19 meters, at least 20 meters, at least 21 meters, at least 22 meters, at least 23 meters, at least 24 meters, at least 25 meters, at least 26 meters, at least 27 meters, at least 28 meters, at least 29 meters, at least 30 meters, at least 31 meters, at least 32 meters, at least 33 meters, at least 34 meters, at least 35 meters, at least 36 meters, at least 37 meters, at least 38 meters, at least 39 meters, at least 40 meters, at least 41 meters, at least 42 meters, at least 43 meters, at least 44 meters, at least 45 meters, at least 46 meters, at least 47 meters, at least 48 meters, at least 49 meters, at least 50 meters, at least 51 meters, at least 52 meters, at least 53 meters, at least 54 meters, at least 55 meters, at least 56 meters, at least 57 meters, at least 58 meters, at least 59 meters, at least 60 meters, at least 61 meters, at least 62 meters, at least 63 meters, at least 64 meters, at least 65 meters, at least 66 meters, at least 67 meters, at least 68 meters, at least 69 meters, at least 70 meters, at least 71 meters, at least 72 meters, at least 73 meters, at least 74 meters, at least 75 meters, at least 76 meters, at least 77 meters, at least 78 meters, at least 79 meters, at least 80 meters, at least 81 meters, at least 82 meters, at least 83 meters, at least 84 meters, at least 85 meters, at least 86 meters, at least 87 meters, at least 88 meters, at least 89 meters, at least 90 meters, at least 91 meters, at least 92 meters, at least 93 meters, at least 94 meters, at least 95 meters, at least 96 meters, or at least 97 meters, at least 98 meters, at least 99 meters, or at least 100 meters. In some embodiments, treatment with an antibody disclosed herein results in an increase of a patient's 6MWD by about 1 meter, about 2 meters, about 3 meters, about 4 meters, about 5 meters, about 6 meters, about 7 meters, about 8 meters, about 9 meters, about 10 meters, about 11 meters, about 12 meters, about 13 meters, about 14 meters, about 15 meters, about 16 meters, about 17 meters, about 18 meters, about 19 meters, about 20 meters, about 21 meters, about 22 meters, about 23 meters, about 24 meters, about 25 meters, about 26 meters, about 27 meters, about 28 meters, about 29 meters, about 30 meters, about 31 meters, about 32 meters, about 33 meters, about 34 meters, about 35 meters, about 36 meters, about 37 meters, about 38 meters, about 39 meters, about 40 meters, about 41 meters, about 42 meters, about 43 meters, about 44 meters, about 45 meters, about 46 meters, about 47 meters, about 48 meters, about 49 meters, about 50 meters, about 51 meters, about 52 meters, about 53 meters, about 54 meters, about 55 meters, about 56 meters, about 57 meters, about 58 meters, about 59 meters, about 60 meters, about 61 meters, about 62 meters, about 63 meters, about 64 meters, about 65 meters, about 66 meters, about 67 meters, about 68 meters, about 69 meters, about 70 meters, about 71 meters, about 72 meters, about 73 meters, about 74 meters, about 75 meters, about 76 meters, about 77 meters, about 78 meters, about 79 meters, about 80 meters, about 81 meters, about 82 meters, about 83 meters, about 84 meters, about 85 meters, about 86 meters, about 87 meters, about 88 meters, about 89 meters, about 90 meters, about 91 meters, about 92 meters, about 93 meters, about 94 meters, about 95 meters, about 96 meters, about 97 meters, about 98 meters, about 99 meters, or about 100 meters.

In some embodiments, treatment with an antibody disclosed herein results in an increase of a patient's 6MWD by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%. In some embodiments, treatment with an antibody disclosed herein results in an increase of a patient's 6MWD by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

In some embodiments, treatment with an antibody disclosed herein results in an increase of a patient's survival by at least 1 month, at least 2 months, at least 3 months, at least 4 months, at least 5 months, at least 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months, at least 23 months, or at least 24 months.

In some embodiments, treatment with an antibody disclosed herein results in an increase of a patient's survival by about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, about 24 months.

In some embodiments, treatment is stopped for a patient with one or more of the following:
- NT-proBNP>8,500 pg/mL, or NT-proBNP is <1800 pg/mL or >8,500 pg/mL
- Troponin-T≤0.03 ng/mL or <0.025 ng/mL
- dFLC<18 mg/dL,
- Absolute neutrophil count (ANC)<$1.0 \times 10^9$/L
- Platelet count<$75 \times 10^9$/L
- Hemoglobin<9 g/dL
- Total bilirubin>2 times the upper limit of normal (xULN)
- Aspartate aminotransferase (AST)/serum glutamic oxaloacetic transaminase (SGOT)>3xULN
- Alanine aminotransferase (ALT)/serum glutamic pyruvic transaminase (SGPT)>3xULN
- Alkaline phosphatase (ALP)>5xULN
- Estimated glomerular filtration rate (eGFR)<30 mL/min/1.73 $m^2$ as estimated by the Chronic Kidney Disease Epidemiology Collaboration (CKD-EPI) equation
- Seated systolic blood pressure <90 or >180 mmHg
- Distance walked during a 6MWT is <30 meters or >550 meters
- Undergoes ASCT or organ transplant
- Myocardial infarction, uncontrolled angina, severe uncontrolled ventricular arrhythmias, or electrocardiographic (ECG) evidence of acute ischemia
- Severe valvular stenosis (e.g. aortic or mitral stenosis with a valve area <1.0 $cm^2$) or severe congenital heart disease
- ECG evidence of acute ischemia or active conduction system abnormalities with the exception of any of the following: First degree AV-block, Second degree AV-block Type 1 (Mobitz Type 1/Wenckebach type), Right or left bundle branch block, and Atrial fibrillation with a controlled ventricular rate (uncontrolled [>110 bpm] ventricular rate is not allowed [determined by an average of three beats in Lead II or three representative beats if Lead II is not representative of the overall EKG])

Peripheral neuropathy assessed as National Cancer Institute-Common Terminology Criteria for Adverse Events (NCI-CTCAE) Grade 2 with pain, Grade 3, or Grade 4

Active malignancy with the exception of any of the following: adequately treated basal cell carcinoma, squamous cell carcinoma, or in situ cervical cancer, adequately treated Stage I cancer from which the subject is currently in remission and has been in remission (e.g. for 2 years), low-risk prostate cancer with Gleason score <7 and prostate-specific antigen <10 mg/mL, and any other cancer from which the subject has been disease-free (e.g. for ≥2 years)

Epilepsy or seizure disorder with the exception of childhood febrile seizures

Suitable antibodies, formulations and treatment regimens for the methods and uses disclosed herein are discussed in greater detail below.

III. Antibodies

The methods of the disclosure include administering to a patient an antibody that specifically bind to immunoglobulin light chain. Examples include antibodies that compete with 11-1F4 for binding to immunoglobulin light chain, and antibodies that compete with 2A4 or 7D8 for binding to human amyloid A peptide, or specifically bind to the same epitope as 11-1F4 (U.S. Pat. No. 8,105,594), 2A4 or 7D8 (U.S. Pat. No. 7,928,203). In some embodiments, the antibody is a humanized version of 2A4. In some embodiments, the antibody is a chimeric or humanized version of 11-1F4, such as, for example, Ch mAb 11-1F4, CAEL-101. In some embodiments, the antibody is one that is disclosed in US20190038745A1, US20200002410A1, and U.S. Pat. No. 10,046,050. In some embodiments, the antibody comprises a light chain variable region comprising three complementarity determining regions set forth as SEQ ID NOs: 3, 4 and 5, and a heavy chain variable region comprising three complementarity determining regions set forth as SEQ ID NOs: 6, 7 and 8. In some embodiments, the light chain variable region comprises the amino acid sequence set forth as SEQ ID NO: 1. In some embodiments, the heavy chain variable region comprises the amino acid sequence set forth as SEQ ID NO: 2.

In other methods, the antibody comprises light chain and heavy chain variable regions of a murine, chimeric, or humanized 2A4 antibody, or of a murine, chimeric, or humanized 7D8 antibody, as described in U.S. Pat. No. 7,928,203 and PCT International Publication No. WO 2009/086539, each of which is incorporated herein by reference in its entirety, and the light chain and heavy chain variable region sequences described in the referenced patent and publication are specifically incorporated by reference herein. Some formulations for the methods disclosed herein are described in U.S. Pat. No. 9,089,529 and PCT International Publication No. WO 2013/063284.

In some embodiments, the antibody comprises a light chain comprising an amino acid sequence set forth as SEQ ID NO: 10 and a heavy chain comprising an amino acid sequence set forth as any one of SEQ ID NOs: 11-13. For example, the antibody can comprise a light chain comprising an amino acid sequence set forth as SEQ ID NO:10 and a heavy chain comprising an amino acid sequence set forth as SEQ ID NO:12. The antibody can include, or not include, the leader sequences of the above-noted light chain and heavy chain amino acid sequences. In some embodiments, the antibody is birtamimab (CAS Registry No. 1608108-91-3).

In other methods, the antibody is a fragment of a 2A4 or 7D8 antibody, including chimeric and humanized versions thereof, such as a Fab fragment, a Fab' fragment, a F(ab')$_2$ fragment, F(ab)c, Dab, nanobody or Fv. As discussed in greater detail below, the antibody can be administered as a pharmaceutical formulation.

IV. Pharmaceutical Formulations and Products

In some embodiments disclosed herein, the antibody can be administered to a patient as a pharmaceutical formulation, for example, comprising in addition to the antibody, a histidine buffer, trehalose, and polysorbate 20. In some such formulations used in the methods described above, the antibody is present at a concentration within the range from about 1 mg/mL to about 100 mg/mL; the histidine buffer is present at a concentration within the range from about 20 mM to about 30 mM; the trehalose is present at a concentration within the range from about 210 mM to about 250 mM; the polysorbate 20 present at a concentration within the range from about 0.005% to about 0.05% by weight; and the pH is within the range from about 6 to about 7. Some suitable formulations for the methods disclosed herein are described in greater detail below.

In some formulations, the antibody is present at a concentration within the range from about 5 mg/mL to about 100 mg/mL. In some formulations, the antibody is present at a concentration within the range from about 5 mg/mL to about 15 mg/mL. In some formulations, the antibody is present at a concentration within the range from about 25 mg/mL to about 75 mg/mL. For example, the antibody may be present at a concentration of about 10 mg/mL, or present at a concentration of about 50 mg/mL. The antibody may be present in a sterile liquid dosage form of about 50 mg/vial to about 500 mg/vial, or greater. For example, the antibody may be present in a sterile liquid dosage form of about 100 mg/vial. In another, non-limiting example, the antibody may be present as a sterile, lyophilized dosage form that may be reconstituted with sterile liquid dosage form of about 500 mg/vial. In another, non-limiting example, the antibody may be present as a sterile, lyophilized dosage form that may be reconstituted with sterile liquid of about 10 mL for a dosage form of about 50 mg/mL or about 500 mg/vial.

Antibodies used in the disclosed formulations can be coupled with a therapeutic moiety, such as a cytotoxic agent, a radiotherapeutic agent, an immunomodulator, a second antibody (e.g., to form an antibody heteroconjugate), or any other biologically active agent that facilitates or enhances the activity of a chimeric or humanized 2A4 or a chimeric or humanized 7D8 antibody. Representative therapeutic moieties include agent known to be useful for treatment, management, or amelioration of amyloid disease or symptoms of amyloid disease.

Therapeutic moieties and/or detectable substances may be coupled or conjugated directly to a murine, chimeric or humanized 2A4 antibody or a murine, chimeric or humanized 7D8 antibody, or indirectly, through an intermediate (e.g., a linker) using techniques known in the art. See e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., Immunol. Rev., 1982, 62:119-58.

Antibodies used in the disclosed formulations also include modified forms of murine, chimeric or humanized 2A4 antibodies, or murine, chimeric or humanized 7D8 antibodies, which have increased in vivo half-lives relative to the corresponding unmodified antibodies. Such modified forms may be prepared, for example, by glycosylation, acetylation, pegylation, phosphorylation, amidation, derivatization by known protecting/blocking groups, proteolytic cleavage, linkage to a cellular ligand or other protein, etc. As one example, representative methods for antibody half-life extension are described in PCT International Publication No. WO 02/060919.

The histidine buffer may be present in some formulations at a concentration of about 25 mM. In some formulations, the histidine buffer comprises L-histidine and L-histidine HCl monohydrate. For example, in some formulations, L-histidine is present at a concentration within the range from about 16 mM to about 22 mM and L-histidine HCl monohydrate is present at a concentration within the range from about 4 mM to about 8 mM.

In some formulations, trehalose is present at a concentration from about 210 mM to about 250 mM, for example, about 230 mM. In some formulations, a different non-reducing sugar is used, such as sucrose, mannitol, or sorbitol.

In some formulations, polysorbate 20 is present at a concentration within the range of about from about 0.005% to about 0.05% by weight, for example, 0.005%, 0.01%, 0.015%, 0.02%, 0.025%, 0.03%, 0.035%, 0.04%, 0.045%, or 0.05%. Alternatively, in some formulations, polysorbate 20 is present at a concentration within the range of about from about 0.05 g/L, 0.1 g/L, 0.15 g/L, 0.2 g/L, 0.25 g/L, 0.3 g/L, 0.35 g/L, 0.4 g/L, 0.45 g/L, or 0.5 g/L. Some formulations include polysorbate 20 at a concentration of 0.2 g/L.

Some formulations are characterized by a pH within the range of about 6-7, for example, a pH of 6.0, 6.1, 6.2, 6.3, 6.4, 6.5, 6.6, 6.7, 6.8, 6.9, or 7.0. Some formulations have a pH of about 6.5. Some formulations are characterized by an osmolality of about 300 mOsm/kg. A bulking agent may also be included some formulations.

Typically, the formulations are sterile, for example, as accomplished by sterile filtration using a 0.2 μm or a 0.22 μm filter. The formulations disclosed herein are also generally stable upon freezing and thawing.

Optionally, formulations disclosed herein may further comprise other excipients, such as saccharides, polyols, and amino acids (e.g., arginine, lysine, and methionine).

The present disclosure also provides formulations substantially free of surfactant, inorganic salts, additional sugars, and/or other excipients, i.e., less than about less than 0.0005%, less than 0.0003%, or less than 0.0001% of such compounds.

An exemplary formulation comprises an antibody comprising a light chain comprising an amino acid sequence set forth as SEQ ID NO: 10 and a heavy chain comprising an amino acid sequence set forth as any one of SEQ ID NOs: 11, 12, or 13, which is present at a concentration of about 50 mg/mL, a histidine buffer present at a concentration of about 25 mM, trehalose present at a concentration of about 230 mM, polysorbate 20 present at a concentration of about 0.2 g/L, and a pH of about 6.5. Some formulations comprise an antibody comprising a light chain comprising an amino acid sequence set forth as SEQ ID NO: 10 and a heavy chain comprising an amino acid sequence set forth as SEQ ID NO: 12, which is present at a concentration of about 50 mg/mL, a histidine buffer present at a concentration of about 25 mM, trehalose present at a concentration of about 230 mM, polysorbate 20 present at a concentration of about 0.2 g/L, and a pH of about 6.5. Some formulations comprise birtamimab, which is present at a concentration of about 50 mg/mL, a histidine buffer present at a concentration of about 25 mM, trehalose present at a concentration of about 230 mM, polysorbate 20 present at a concentration of about 0.2 g/L, and a pH of about 6.5.

The methods disclosed herein involve pharmaceutical products comprising lyophilized antibody drug substance and instructions for reconstitution and use. For example, a representative pharmaceutical product can comprise: (a) a vial comprising about 100 mg antibody in powder form; (b) instructions for reconstitution of the antibody; and (c) instructions for preparing the reconstituted antibody for infusion, wherein (i) the antibody comprises a light chain comprising an amino acid sequence set forth as SEQ ID NO: 10 and a heavy chain comprising an amino acid sequence set forth as any one of SEQ ID NOs: 12-15; and (ii) the reconstitution instructions require reconstitution with water for injection to an extractable volume of 10 mL.

IV. Treatment Regimens

As used herein, the terms "treat" and "treatment" refer to the alleviation or amelioration of one or more symptoms or effects associated with the disease, prevention, inhibition or delay of the onset of one or more symptoms or effects of the disease, lessening of the severity or frequency of one or more symptoms or effects of the disease, and/or increasing or trending toward desired outcomes as described herein.

Desired outcomes of the treatments disclosed herein vary according to the amyloid disease and patient profile and are readily determinable to those skilled in the art. Desired outcomes include an improvement in the patient's health status. Generally, desired outcomes include measurable indices such as reduction or clearance of pathologic amyloid fibrils, decreased or inhibited amyloid aggregation and/or deposition of amyloid fibrils, and increased immune response to pathologic and/or aggregated amyloid fibrils. Desired outcomes also include amelioration of amyloid disease-specific symptoms. For example, desired outcomes for the treatment of AL amyloidosis include a decrease in the incidence or severity of known symptoms, including organ dysfunction, peripheral and autonomic neuropathy, carpal tunnel syndrome, macroglossia, restrictive cardiomyopathy, arthropathy of large joints, immune dyscrasias, myelomas, as well as occult dyscrasias.

For example, the 6-minute walk test (6MWT) can be a surrogate endpoint used to assess cardiac functional response (Pulido et al., The six-minute walk test in patients with AL amyloidosis: a single centre case series, British Journal of Haematology, 2017, 177, 388-394). It measures the distance patients can walk in 6 minutes along thirty meter long hallways. For example, the mean 6-minute walk distance (6MWD) of AL amyloidosis patients with cardiac involvement has been shown to be significantly shorter than the distance walked by AL amyloidosis patients without cardiac involvement. Further, increased distance walked is correlated with a decrease in mortality. A positive change in health-related quality of life is also a desired outcome of the disclosed therapies, including, for example, as measured by the SF-36 Health Survey (White et al., Psychometric validation of the SF-36 Health Survey in light chain amyloidosis: results from community-based and clinic-based samples, *Patient Related Outcome Measures* 2017:8 157-167). The SF-36 involves scores that represent eight dimensions of function and well-being: physical functioning, role limitations due to physical problems, bodily pain, general health perceptions, vitality, social functioning, role limitations due to emotional problems and mental health, and summary scores, such as physical component summary (PCS) and mental component summary (MCS). Higher SF-36 scores represent better health. Desired outcomes of the disclosed therapies are generally quantifiable measures as compared to a control or baseline measurement. As used herein, relative terms such as "improve," "increase," or "reduce" indicate values relative to a control, such as a measurement in the same individual prior to initiation of treatment described herein, or a measurement in a control individual or group. A control individual is an individual afflicted with the same amyloid disease as the individual being treated, who is about the same age as the individual being treated (to ensure that the stages of the disease in the treated individual and the control individual are comparable), but who has not received treatment using the disclosed antibody formulations. In this case, efficacy of the disclosed antibody formulations is assessed by a shift or trend away from measurable indices in the untreated control. Alternatively, a control individual is a healthy individual, who is about the same age as the individual being treated. In this case, efficacy of the disclosed antibody formulations is assessed by a shift or trend toward from measurable indices in the healthy control. Changes or improvements in response to therapy are generally statistically significant and described by a p-value less than or equal to 0.1, less than 0.05, less than 0.01, less than 0.005, or less than 0.001 may be regarded as significant.

Treatment typically entails multiple dosages over a period of time. Treatment can be monitored by assaying antibody, or employing radiolabeled SAP Scintigraphy over time. If the response falls, a booster dosage may be indicated. Changes in the health status of the patients can be monitored based on outcome measures such as 6MWD, SF-36 PCS (SF-36v2), hospitalizations and survival as discussed in greater detail above. In addition, the response of patients with AL amyloidosis to treatment can be monitored by assessing cardiac markers, such as NT-proBNP and/or troponin-T, serum creatine, and/or alkaline phosphatase; by performing serum free light chain (SFLC) assays, quantitative immunoglobulin assays, biopsies, serum protein electrophoresis (SPEP), urine protein electrophoresis (UPEP), serum, urine immunofixation electrophoresis (IFE), and/or organ imaging techniques. An exemplary complete response (CR) can be determined from response criteria including negative IFE of serum and urine, normal κ/λ, ration and/or <5% plasma cells in bone marrow. An exemplary very good partial response (VGPR) can be determined from a dFLC of <40 mg/L. An exemplary partial response (PR) can be determined from a dFLC decrease of ≥50%. In the kidney, a response to treatment can be determined, for example, from a ≥50% reduction (e.g., >0.5 g/24 hours) in 24 hour urine protein excretion in the absence of either a reduction in eGFR of ≥25% or an increase in serum creatine of >0.5 mg/dL. In the liver, a response to treatment can be determined, for example, from a ≥50% reduction in initially elevated alkaline phosphatase or a ≥2 cm reduction in liver size on CT scan or MM. In the heart, a response to treatment can be determined, for example, from a >30% and >300 ng/L reduction in NT-proBNP in patients with baseline of NT-proBNP of >650 ng/L. In the kidney, a response to treatment can be determined, for example, from a >30% decrease in proteinuria or a decrease in proteinuria to <0.5 g/24 hours in the absence of renal progression. Neuropathy responders are generally characterized by <2 point increase in NIS-LL from baseline. Improvement in neuropathy (e.g., improved nerve function) is determined from a decrease in the NIS-LL from baseline. Improvement in health status can also be determined from a decrease in the frequency of hospitalizations, a decrease in hospitalizations of greater than ninety days, or from longer survival relative to an untreated different patient with a similar prognosis upon diagnosis, for example, AL amyloidosis patients with cardiac involvement.

The antibody formulation can be administered intravenously or subcutaneously in dosage ranges from about 0.5 mg/kg to about 30 mg/kg of the host body weight. For example, dosages can be about 0.5 mg/kg body weight, about 1.0 mg/kg, about 1.5 mg/kg, about 2.0 mg/kg, about 4.0 mg/kg, about 5.0 mg/kg, about 8.0 mg/kg, about 10 mg/kg, about 15 mg/kg, about 16 mg/kg, about 20 mg/kg, about 24 mg/kg, about 25 mg/kg, or about 30 mg/kg body weight. The dosages can also be administered according to body surface area from about 0.5 mg/m2 to about 500 mg/m2, for example, 0.5, 5, 10, 50, 100, 250 or 500 mg/m2. For intravenous dosing, an amount of the antibody formulation sufficient to achieve the desired dosage for the individual patient is transferred from one or more vials to one or more intravenous bags containing a liquid (e.g., saline) and administered to the patient.

Antibody is usually administered on multiple occasions. An exemplary treatment regimen entails administration once per every two weeks, once a month, or once every 3 to 6 months. For example, patients can receive the antibody formulation once every four weeks as a cycle, for example every twenty-eight days. The dosing frequency can be adjusted depending on the pharmacokinetic profile of the antibody formulation in the patient. For example, the half-life of the antibody may warrant a two week frequency of dosing. In some embodiments, the pharmaceutical formulation is administered intravenously every 28 days with an antibody dosage of about 24 mg/kg. For example, some patients may receive an intravenous dose of about 24 mg/kg birtamimab every 28 days. For example, some patients may receive an intravenous dose of about 24 mg/kg birtamimab every 28 days (±5 days). In certain embodiments, a minimum of 21 days is required between doses. For some such patients, the birtamimab formulation transferred to the intravenous bag was first reconstituted from a lyophilized formulation to a formulation having a pH of about 6.5 and comprising about 50 mg/ml birtamimab, about 25 mM histidine buffer, about 230 mM trehalose and about 0.2 g/L polysorbate 20. For some patients the desired dosage can be administered subcutaneously without dilution from a vial containing any of the formulations disclosed herein.

In some embodiments disclosed herein, the antibody is administered to the patient for at least 8 months, at least 9 months, at least 10 months, at least 11 months, at least 12 months, or for a longer period of time. For example, the pharmaceutical formulation is administered to the patient for a duration effective to achieve or maintain an improvement in health status as indicated by an increase in 6MWD or SF-36 PCS score, or long enough to achieve or maintain a lower risk of mortality relative to an untreated patient. For some patients, the lower risk can be established after at least 8 months of treatment. For some patients, the lower risk can be established after at least 9 months of treatment. For some patients, the lower risk can be established after at least 12 months of treatment or after at least 18 months of treatment or after twenty-four months of treatment. For these patients, a lower risk of mortality correlates with longer survival times relative to untreated patients.

Also disclosed herein are combination therapies for treatment or prophylaxis of AL amyloidosis. Such combination therapies are performed by administering an antibody formulation disclosed herein in conjunction with one or more second therapeutic agents, such as another therapy to treat or effect prophylaxis of AL amyloidosis. Combination therapies as disclosed herein may also be performed in conjunction with a second therapy is used to treat or effect prophylaxis of a disease or condition associated with amyloid disease, such as an inflammatory disease, a chronic microbial infection, a neoplasm (including malignant neoplasms), an inherited inflammatory disease, and/or a lymphoproliferative disorder. Numerous treatments are available in commercial use, in clinical evaluation, and in pre-clinical development, any of which could be selected for use in combination with the disclosed antibody formulations. Such treatments can be one or more compounds or treatments selected from, but not limited to several major categories, namely, (i) non-steroidal anti-inflammatory drugs (NSAIDs; e.g., detoprofen, diclofenac, diflunisal, etodolac, fenoprofen, flurbiprofen, ibuprofen, indomethacin, ketoprofen, meclofenameate, mefenamic acid, meloxicam, nabumeone, naproxen sodium, oxaprozin, piroxicam, sulindac, tolmetin, celecoxib, rofecoxib, aspirin, choline salicylate, salsalte, and sodium and magnesium salicylate); (ii) steroids (e.g., cortisone, dexamethasone, hydrocortisone, methylprednisolone, prednisolone, prednisone, triamcinolone); (iii) DMARDs, i.e., disease modifying antirheumatic drugs (e.g., cyclosporine, azathioprine, methotrexate, leflunomide, cyclophosphamide, hydroxychloroquine, sulfasalazine, D-penicillamine, minocycline, and gold); (iv) recombinant proteins (e.g., ENBREL® (etanercept, a soluble TNF receptor) and REMICADE® (infliximab) a chimeric monoclonal anti-TNF antibody); (v) stem cell transplantation; and/or (vi) chemotherapy. Patients with AL amyloidosis may also receive treatment regimens that include drugs or combinations of drugs often used to treat hematological malignancies, such as melphalan, prednisone, dexamethasone, lenalidomide (REVLIMID®), proteosome inhibitors such as bortezomib (VELCADE®) and carfilzomib (KYPROLIS®), and CD38 agents such as daratumumab (DARZALEX®), at dosages in the range of the standard of care.

When performing a combination therapy, the two or more drug substances are administered simultaneously or sequentially in any order, i.e., a formulation disclosed herein is administered prior to administering a second drug substance, concurrently with a second drug substance, or subsequent to administration of a second drug substance. For example, a combination therapy may be performed by administering a first therapy prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) administering a second agent/therapy.

The dosage, frequency and mode of administration of each component of the combination can be controlled independently. For example, one therapeutic agent/therapy may be administered orally three times per day, while the second therapeutic agent/therapy may be administered intramuscularly once per day. Combination therapy may be given in on-and-off cycles that include rest periods. The compounds may also be admixed or otherwise formulated together such that one administration delivers both compounds. In this case, each therapeutic agent is generally present in an amount of 1-95% by weight of the total weight of the composition. Alternatively, an antibody formulation disclosed herein and a second therapeutic agent can be formulated separately and in individual dosage amounts. Drug combinations for treatment can be provided as components of a pharmaceutical pack.

Preferably, the disclosed combination therapies elicit a synergistic therapeutic effect, i.e., an effect greater than the sum of their individual effects or therapeutic outcomes. Measurable therapeutic outcomes are described herein. For example, a synergistic therapeutic effect may be an effect of at least about two-fold greater than sum of the therapeutic effects elicited by the single agents of a given combination, or at least about five-fold greater, or at least about ten-fold greater, or at least about twenty-fold greater, or at least about fifty-fold greater, or at least about one hundred-fold greater. A synergistic therapeutic effect may also be observed as an increase in therapeutic effect of at least 10% compared to the sum of the therapeutic effects elicited by the single agents of a given combination, or at least 20%, or at least 30%, or at least 40%, or at least 50%, or at least 60%, or at least 70%, or at least 80%, or at least 90%, or at least 100%, or more. A synergistic effect is also an effect that permits reduced dosing of therapeutic agents when they are used in combination.

Some methods of the disclosure include treating a subject having AL amyloidosis by determining one or more of the following prognostic indicators: (1) the Mayo Stage of the patient's AL amyloidosis, (2) the 6 minute walk distance (6MWD) and ejection fraction (EF) of the patient, and/or the Mayo Stage and the EF of the patient. Once the prognostic indicator(s) has been determined, a patient is selected the patient for treatment if the patient meets one of the following treatment criteria: (1) has Mayo Stage IV AL amyloidosis; (2) has a 6MWD≥150 meters and an EF>50% at baseline; (3) has Mayo Stage IV and EF>50% at baseline; or (4) has Mayo Stage IV, a 6MWD≥150 meters and an EF>50% at baseline. Treatment includes administering an effective dosage of an antibody disclosed herein.

In one method of the disclosure, a patient meeting or more of the prognostic indicators is treated with birtamimab (24 mg/kg) supplied as a sterile, lyophilized dosage form in a 20/25 mL vial containing 500 mg birtamimab. Each vial may be reconstituted with 9.6 mL sterile water for injection (WFI) to a concentration of 50 mg/mL resulting in a buffered, isotonic, preservative-free solution. Birtamimab is administered once every 28 days as an initial 120 (±10)-minute IV infusion. If the subject tolerates the initial infusion, subsequent infusions may be administered over 60 (±10) minutes. Dose are administered at intervals of at least 21 days.

Patients may also be treated with concomitant standard of care chemotherapy, which may include, for example, bortezomib administered subcutaneously on a weekly basis.

EXAMPLES

The following examples have been included to illustrate modes disclosed herein. Certain aspects of the following examples are described in terms of techniques and procedures found or contemplated by the present co-inventors to work well in the practice disclosed herein. In light of the present disclosure and the general level of skill in the art, those of skill appreciate that the following examples are intended to be exemplary only and that numerous changes, modifications, and alterations may be employed without departing from the scope of the disclosure.

Example 1

Phase 2b Clinical Assessment of NEOD001, Also Known as Birtamimab (Humanized 2A4)

A Phase 2b global, multi-center, randomized, double-blind, placebo-controlled clinical study of NEOD001 vs. placebo was conducted in previously-treated patients with AL amyloidosis and persistent cardiac dysfunction (PRONTO Study). The study enrolled 129 patients. Patients were randomized on a 1:1 basis to receive 24 mg/kg of NEOD001 (n=66) or placebo (n=63) via intravenous infusion every 28 days. The primary outcome measure was cardiac best response as measured by NT-proBNP through 12 months of treatment. Secondary outcome measures included change in Short Form-36 (SF-36 Questionnaire, change in 6 minute walk test (6MWT), renal best response as measured by proteinuria, change in Neuropathy Impairment Score-Lower Limb (NIS-LL) score and NT-proBNP slope. Additional information regarding the clinical study design is available on https://clinicaltrials.gov. The PRONTO Study did not meet its primary or secondary endpoints.

Example 2

Phase 3 Clinical Assessment of NEOD001

A Phase 3 global, multi-center, randomized, double-blind, placebo-controlled clinical study of NEOD001 vs. placebo was conducted in newly diagnosed, treatment-naïve patients with AL amyloidosis and cardiac dysfunction, with both arms of the study receiving standard of care (VITAL Study; The VITAL Amyloidosis Study, a Global Phase 3, Efficacy and Safety Study of NEOD001 in Patients With AL Amyloidosis (VITAL), ClinicalTrials.gov Identifier: NCT02312206). The study enrolled 260 patients (see Table 1).

TABLE 1

| | All Subjects (n = 260) | | Mayo Stage IV Subjects (n = 77) | |
|---|---|---|---|---|
| | NEOD001 + SOC (n = 130) | Placebo + SOC (n = 130) | NEOD001 + SOC (n = 38) | Placebo + SOC (n = 39) |
| Age, median (Q1, Q3) | 64.2 (57.6, 70.9) | 62.6 (57.0, 69.3) | 63.56 (55.71, 69.78) | 63.74 (56.97, 68.40) |
| Gender (male), n (%) | 82 (63) | 90 (69) | 25 (65.8) | 28 (71.8) |
| Ethnicity, n (%) | | | | |
| Hispanic or Latino | 2 (1.5) | 2 (1.5) | 0 | 0 |
| Not Hispanic or Latino | 116 (89.2) | 122 (93.8) | 34 (89.5) | 36 (92.3) |
| Not provided or unknown | 12 (9.2) | 6 (4.6) | 4 (10.5) | 3 (7.7) |
| Race, n (%) | | | | |
| White | 118 (90.8) | 120 (92.3) | 36 (94.7) | 36 (92.3) |
| Black or African American | 9 (6.9) | 3 (2.3) | 2 (5.3) | 2 (5.1) |
| Asian | 2 (1.5) | 2 (1.5) | 0 | 0 |
| Other | 1 (0.8) | 5 (3.8) | 0 | 1 (2.6) |
| Age at AL amyloidosis diagnosis (years), median (Q1, Q3) | 64.10 (57.51, 70.91) | 62.41 (56.83, 69.29) | 63.48 (55.61, 69.66) | 63.75 (56.83, 68.47) |
| Duration since AL amyloidosis diagnosis (months), median (Q1, Q3) | 1.31 (0.92, 1.87) | 1.48 (0.95, 2.17) | 1.15 (0.69, 1.58) | 1.45 (0.89, 1.81) |
| Number of derived involved organs at baseline, median (Q1, Q3) | 2.0 (1.0, 2.0) | 1.0 (1.0, 2.0) | 1.0 (1.0, 2.0) | 1.0 (1.0, 2.0) |
| Screening NT-proBNP ≥1800 pg/mL, n (%) | 95 (73.1) | 100 (76.9) | 38 (100) | 39 (100) |
| Baseline NT-proBNP (pg/mL), median (Q1, Q3) | 3146 (1650, 5173) | 3184 (1910, 5551) | 5142 (3228, 5939) | 5415 (4054, 8073) |
| Baseline troponin-T (ng/mL), median (Q1, Q3) | 0.03 (0.03, 0.06) | 0.03 (0.03, 0.08) | 0.05 (0.04, 0.09) | 0.09 (0.06, 0.13) |
| Baseline FLC ratio, median (Q1, Q3) | 0.10 (0.03, 0.32) | 0.11 (0.04, 0.51) | | 0.05 (0.03, 11.14) |
| Baseline dFLC$^a$ (mg/dL), median (Q1, Q3) | 26.31 (13.83, 53.05) | 38.18 (18.00, 63.06) | 44.44 (25.13, 56.17) | 57.42 (35.52, 106.28) |
| Mayo stage, n (%) | | | | |
| I | 11 (4) | 10 (4) | 0 | 0 |
| II | 34 (13) | 28 (11) | 0 | 0 |
| III | 47 (18) | 53 (20) | 0 | 0 |
| IV | 38 (15) | 39 (15) | 38 (100) | 39 (100) |

$^a$Baseline dFLC is only calculated for subjects with an abnormal baseline FLC ratio (Kappa/Lambda <0.26 or >1.65) and is defined as the difference between involved and uninvolved FLCs.
dFLC, difference between involved minus uninvolved serum free light chains; FLC, free light chain; NT-proBNP, N-terminal pro-brain natriuretic peptide; SOC standard of care.

Patients were randomized on a 1:1 basis to receive 24 mg/kg of NEOD001 or placebo via intravenous infusion every 28 days. All patients received bortezomib based chemotherapy concurrently with NEOD001 or placebo. Placebo was administered as a 250 mL bag of normal saline once every 28 days. The primary outcome measures were time to composite of all-cause mortality or cardiac hospitalization. Secondary outcome measures included NT-proBNP best response, time to cardiac mortality or cardiac hospitalization, change in the 6 minute walk test, change in the Short Form-36 questionnaire, change in the Kansas City Cardiomyopathy questionnaire, renal best response as assessed using Palladini et al, 2014 criteria and hepatic best response as assessed using Comenzo et al, 2012 criteria. Additional information regarding the clinical study design is available on https://clinicaltrials.gov. Based on the results from the PRONTO Study, a futility analysis was performed on the ongoing VITAL Study. The futility analysis, based on 103 adjudicated events of the 156 events specified to complete the study, was not statistically significant. The hazard ratio (HR) was 0.84 favoring NEOD001 vs. control arm (HR, 0.84, 95% confidence interval [CI], 0.57-1.204; P=0.386). Based on the results from the PRONTO Study and the futility analysis of the VITAL Study, clinical development of NEOD001 was discontinued.

Example 3

Statistical Analysis of VITAL Study—Surprising Results in Certain Patients

Figure 5:
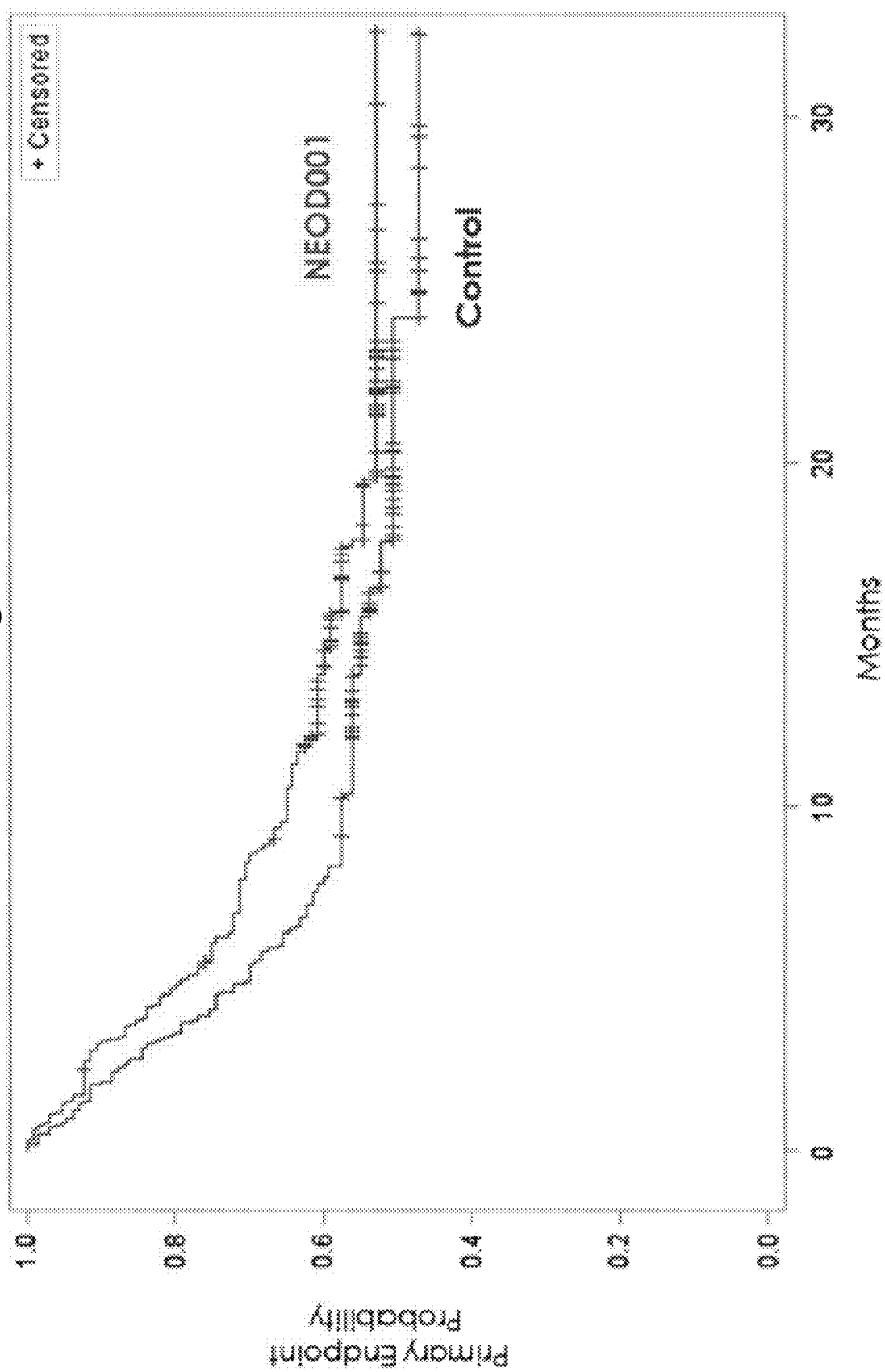
FIG. 5 shows Kaplan-Meier Estimate of Primary Composite Endpoint of Time to ACM or CH.

Following the discontinuation of NEOD001 development, statistical analysis analysis was performed on the VITAL Study data, which necessarily includes censored data due to the study termination. The data was censored at twelve months. The final study results were consistent with the futility analysis. NEOD001 was not significantly different from control for the primary endpoint of all-cause mortality or cardiac hospitalization 91 days) (HR, 0.835; 95% CI 0.5799-1.2011; P=0.330; see Table 2; and FIG. 5). Nor was NEOD001 significantly different from control for any key secondary endpoints (SF-36 PCS, 6MWD, NT-proBNP best response, or renal best response). Subsequent post hoc analyses for subjects categorized as Mayo Stage IV yielded an even stronger result favoring birtamimab (HR=0.538), revealing a potential survival benefit for this subset of patients.

Figure 6:
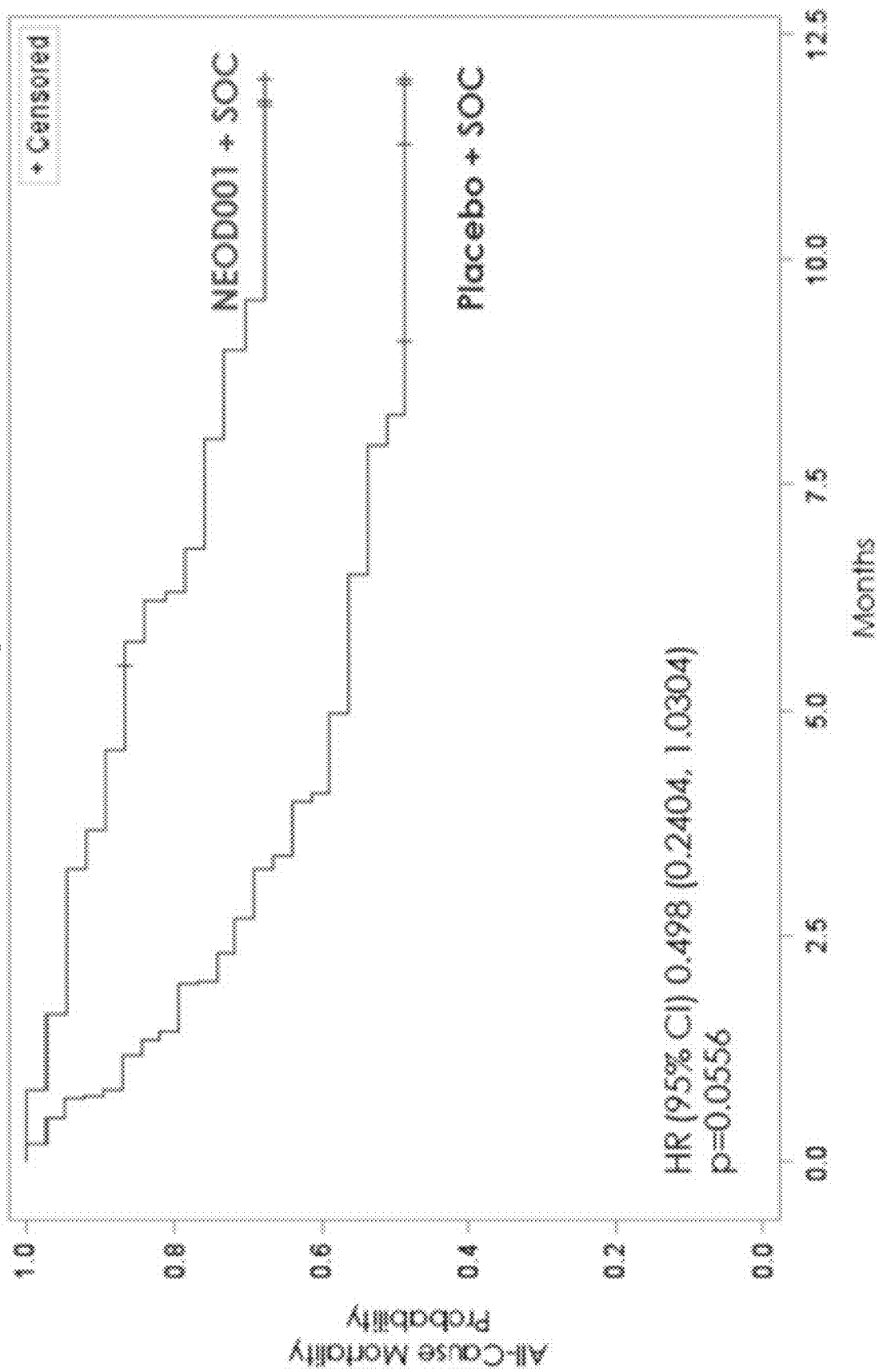
FIG. 6 shows Kaplan-Meier Estimate of ACM in Stage IV (mITT).

Surprisingly, analysis of the data suggested an improvement in health status in certain subsets of patients, namely Mayo Stage IV patients (n=77 of 260; approximately 30% of the patients enrolled in the VITAL study were Mayo stage IV) and patients having a baseline 6MWD of greater than 150 meters and an ejection fraction of greater than 50% regardless of Mayo stage (n=135). The hazard ratios for such patient subpopulations were 0.498 and 0.511, respectively, in favor of treatment, as the median overall survival in stage IV (mITT) was 8.3 months in the placebo+SOC group and was not reached (>12 months) in the NEOD001+SOC group (see FIG. 6). Further, the observed benefit appears to be further enhanced for Mayo Stage IV patients with baseline 6MWD of ≥150 meters and an ejection fraction (EF) of >50% (n=36). The hazard ratio for such patients was 0.201 in favor of treatment. In addition, a benefit was also observed in Mayo Stage IV patients with an ejection fraction (EF) of >50% (n=37), without regard to 6MWD. It is surprising that greater improvement was observed in Mayo Stage IV patients than in Stage I-III patients because it is generally accepted that treatment intervention at earlier stages of diseases associated with amyloid burden is required to achieve an improvement.

Example 4

Response of Mayo Stage IV Patients

Figure 1B:
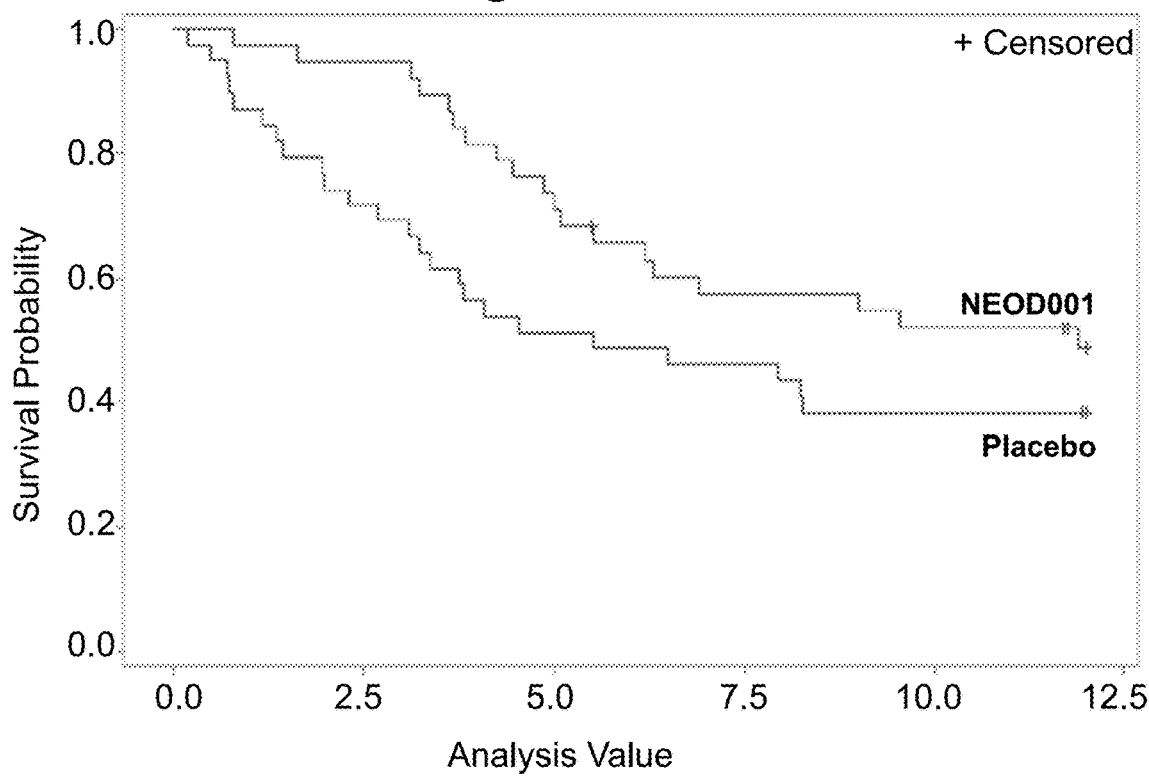

As shown in FIGS. 1A and 1B, Mayo Stage IV patients treated with NEOD001 demonstrated a greater improvement in health status, as measured by the composite of all-cause mortality or cardiac hospitalization for more than 91 days through 12 months, relative to patients treated with placebo, compared to the difference seen with Stage I-III patients, with Stage IV patient results having an HR of 0.635 (36.5% relative risk reduction) with p=0.1409 (FIG. 1B) as compared to 0.879 (12.15% relative risk reduction) with p=0.6125 for Stage I-III patients (FIG. 1A).

Figure 2A:
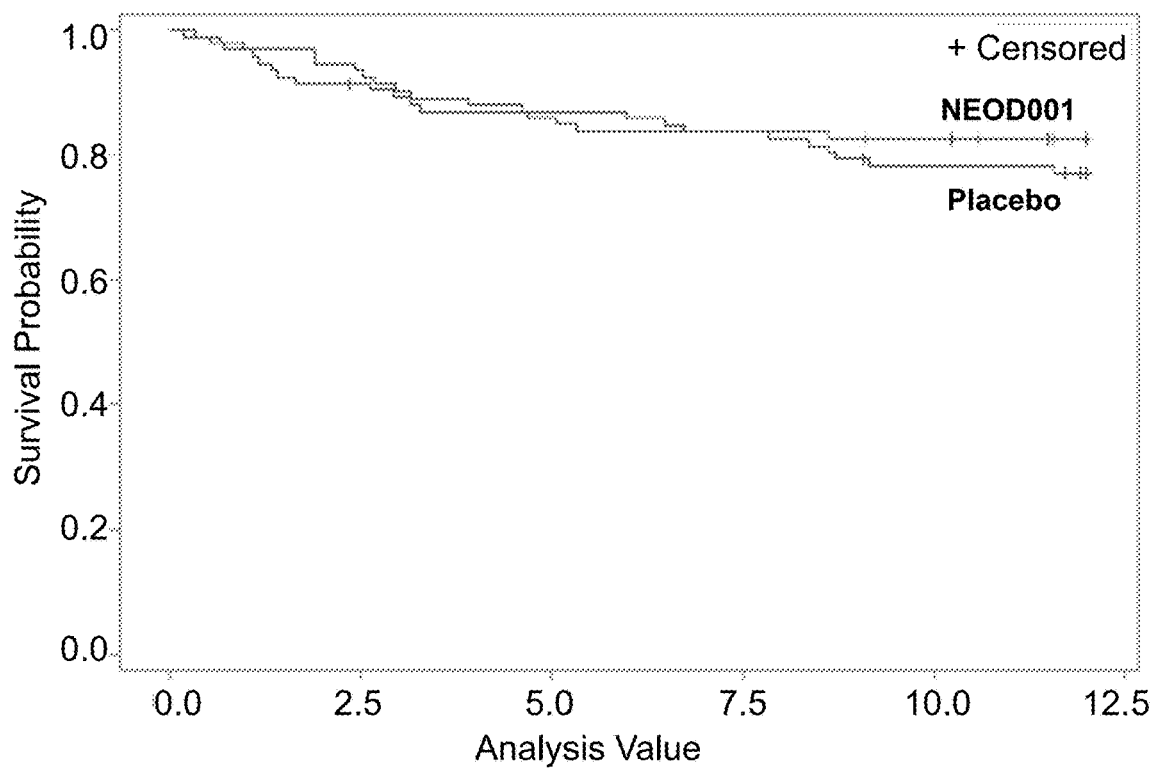
FIGS. 2A-2B show the all-cause mortality in AL amyloidosis patients treated with NEOD001 vs placebo in Mayo Stage I-III patients (FIG. 2A) and Mayo Stage IV patients (FIG. 2B), respectively.
Figure 2B:
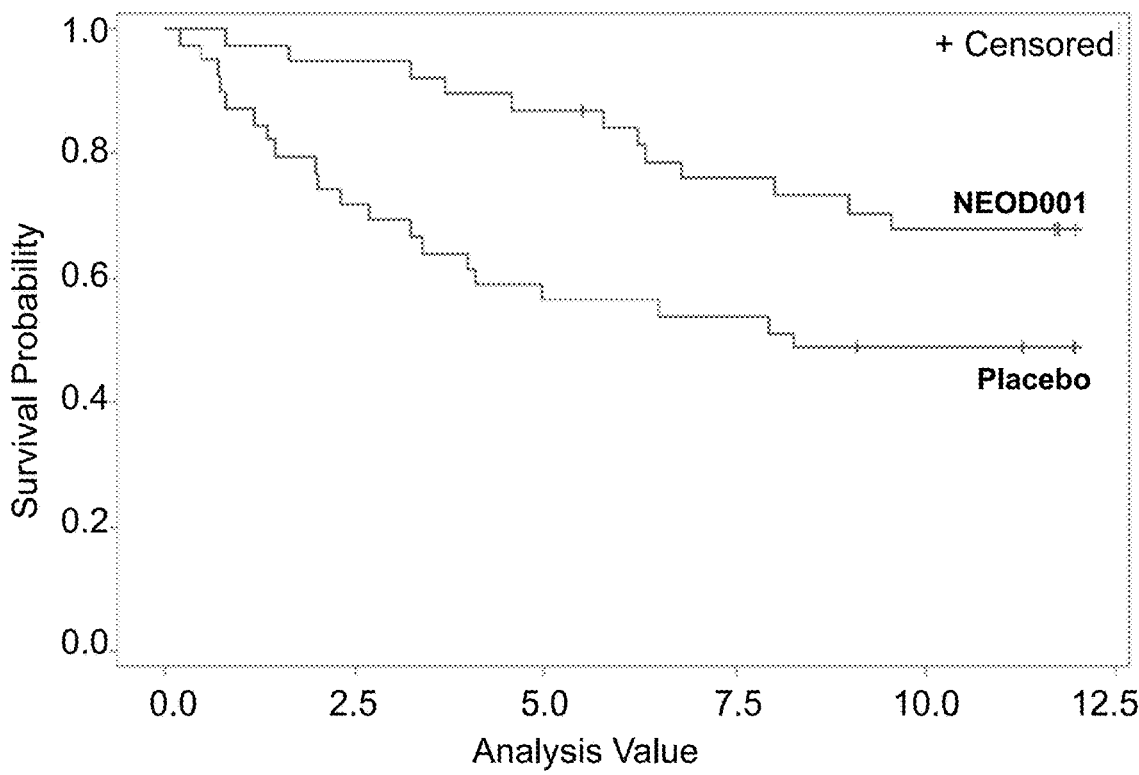

As shown in FIGS. 2A and 2B, Stage IV patients treated with NEOD001 demonstrated a greater improvement in health status, as measured by all-cause mortality through 12 months, relative to patients treated with placebo, compared to the difference seen with Stage I-III patients, with Stage IV patient results having an HR of 0.498 (50.2% relative risk reduction) with p=0.0556 (FIG. 2B) as compared to 1.244 (−24.4% relative risk reduction) with p=0.5159 for Stage I-III patients (FIG. 2A).

TABLE 2

| | | ITT and mITT Results | | |
|---|---|---|---|---|
| Mayo Stage | Endpoint[a,b] | N | ITT HR[c] (95% CI) P-value[d] | mITT[e] (12-months) HR[c] (95%CI) P-value[d] |
| All | Composite primary endpoint | 260 | 0.835 (0.5799-1.2011) P = 0.3300 | 0.784 (0.5341-1.1507) P = 0.2129 |
| Stage I-III | All-cause mortality | 183 | 1.334 (0.7386-2.4107) P = 0.3375 | 1.244 (0.6435-2.4035) P = 0.5159 |
| Stage IV | All-cause mortality | 77 | 0.544 (0.2738-1.0826) P = 0.0787 | 0.498 (0.2404-1.0304) P = 0.0556 |

[a]Composite primary endpoint = all-cause mortality or cardiac hospitalization (>90 days).
[b]All-cause mortality regardless of cardiac hospitalization.
[c]HR <1.0 in favor of NEOD001 + SOC; HR >1.0 in favor of placebo + SOC.
[d]All P-values other than for the composite primary endpoint for the ITT analysis are descriptive; P-value derived from log rank test.
[e]mITT = initial 12-month time period. CI, confidence interval; HR, hazard ratio; ITT, intent-to-treat; mITT, modified intent-to-treat.

Figure 3A:
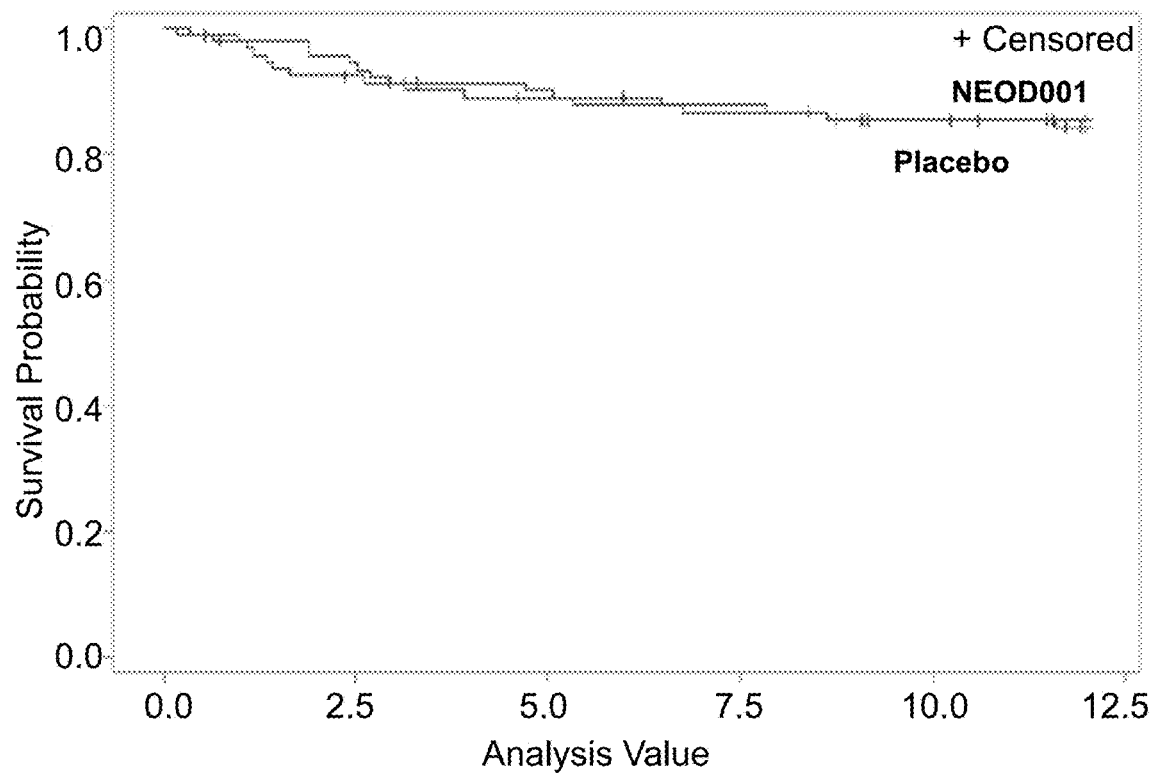
FIGS. 3A-3B show the cardiac mortality through 12 months in AL amyloidosis patients treated with NEOD001 vs placebo in Mayo Stage I-III patients (FIG. 3A) and Mayo Stage IV patients (FIG. 3B), respectively.
Figure 3B:
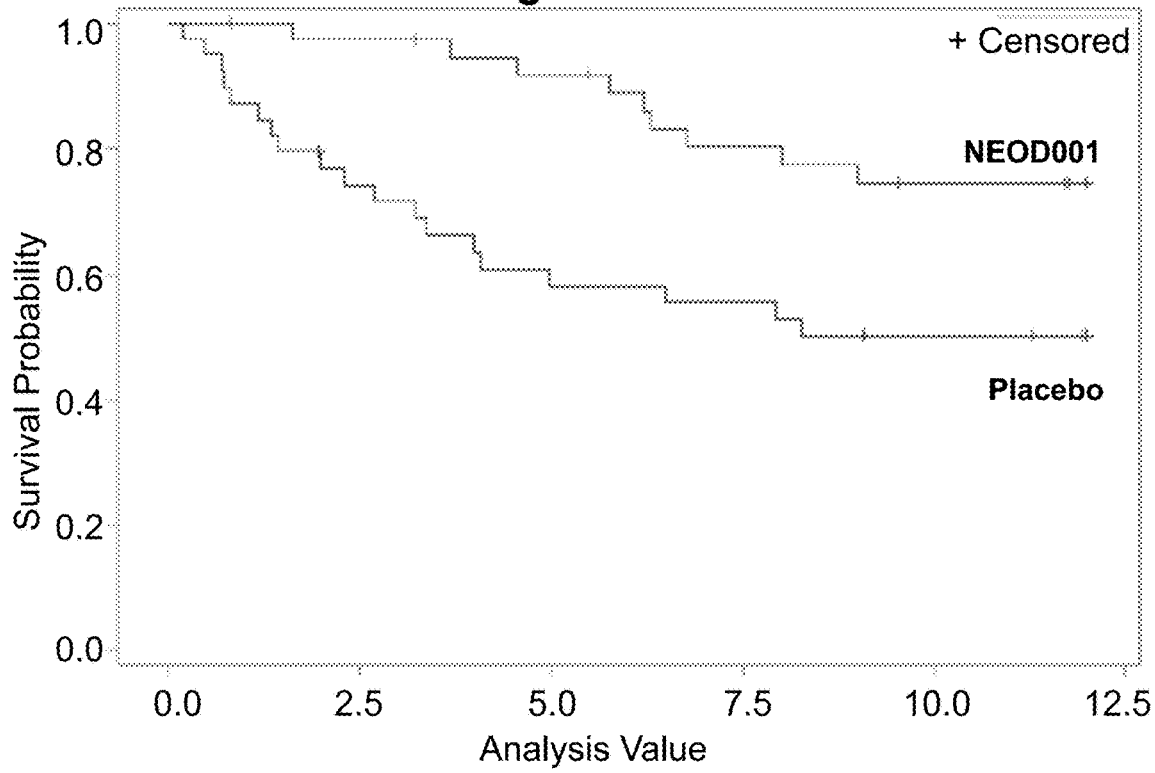

As shown in FIGS. 3A and 3B, Stage IV patients treated with NEOD001 demonstrated a greater improvement in health status, as measured by cardiac mortality through 12 months relative to patients treated with placebo, compared to the difference seen with Stage I-III patients, with Stage IV patient results having an HR of 0.378 (62.2% relative risk reduction) with p=0.0142 (FIG. 3B) as compared to 1.051 (−5.1% relative risk reduction) with p=0.8971 for Stage I-III patients (FIG. 3A).

Figure 7:
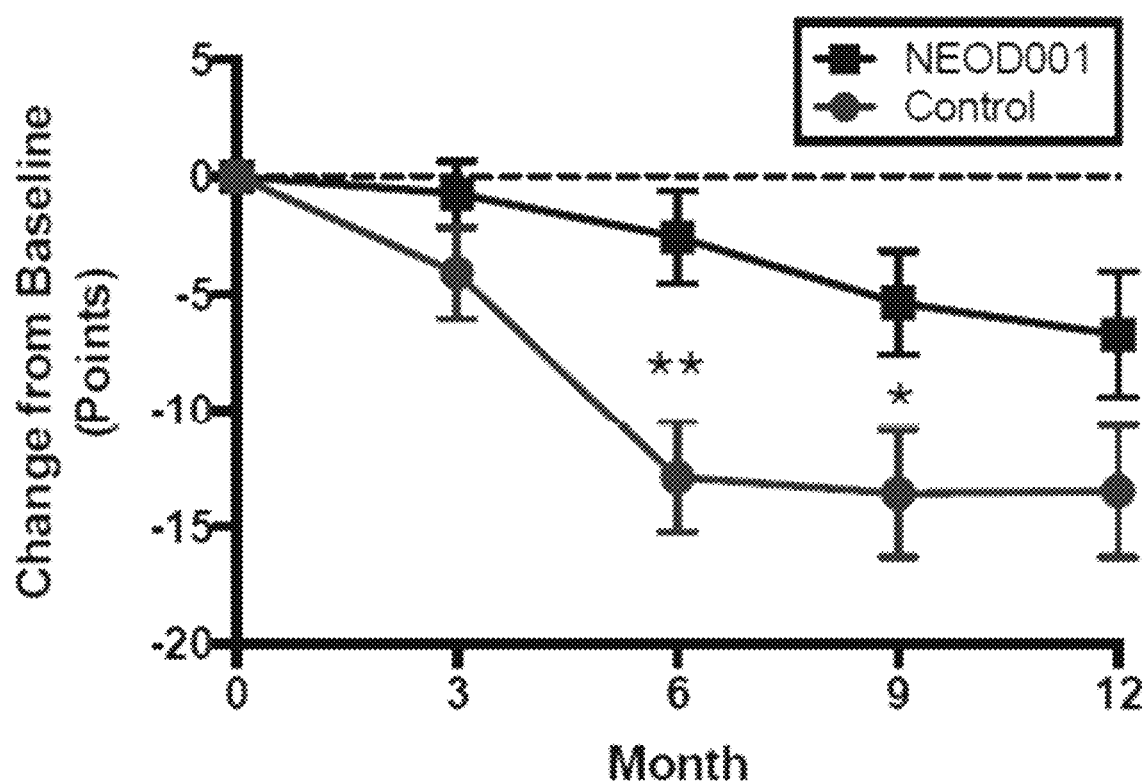
FIG. 7 shows change from baseline in SF-36 PCS Scores for Mayo Stage IV Subjects (mITT). *P<0.05 and **P<0.005 using Student's t-test, comparing change from baseline between treatment groups. Error bars=standard error of the mean (SEM). mITT, modified intent-to-treat; SE, standard error; SF-36 PCS, Short Form-36 Physical Component Summary; SOC, standard of care.

As shown in Table 3, Stage IV patients treated with NEOD001 demonstrated a greater improvement in health status, as measured by SF-36 PCS score change from baseline to Month 9, relative to patients treated with placebo, compared to the difference seen with Stage I-III patients, with Stage IV patient having a change of +5.54 points with p=0.0258 as compared to a change of −0.65 with p=0.7150 for Stage I-III patients. Abbreviations: LSM (Least Squares Mean); SE (Standard Error); CI (Confidence Interval). In the mITT analysis, SF-36 PCS scores showed significantly less deterioration from baseline to 6 months (P<0.05) and 9 months (P<0.005) in the NEOD001+SOC group compared with the placebo+SOC group (see FIG. 7), and change from baseline in 6MWD was significantly greater at all time points through month 12 in the NEOD001+SOC group versus the placebo+SOC group.

TABLE 3

SF-36 PCS Score Change from Baseline to Month 9

|  |  | NEOD001 | Control | Difference | p-value |
|---|---|---|---|---|---|
| Stage I-III | N Month 9 | 92 | 91 | | |
|  | LSM (SE) | 32.52 (1.37) | 33.17 (1.36) | | |
|  | 95% CI | 29.83, 35.20 | 30.50, 35.84 | | |
|  | Change from Baseline | | | | |
|  | LSM (SE) | −3.47 (1.37) | −2.82 (1.36) | −0.65 (1.79) | |
|  | 95% CI | −6.16, −0.79 | −5.49, −0.15 | −4.16, 2.86 | 0.7150 |
| Stage IV | N Month 9 | 38 | 39 | | |
|  | LSM (SE) | 34.55 (3.58) | 29.01 (3.47) | | |
|  | 95% CI | 27.53, 41.57 | 22.21, 35.80 | | |
|  | Change from Baseline | | | | |
|  | LSM (SE) | 3.40 (3.58) | −2.14 (3.47) | 5.54 (2.48) | |
|  | 95% CI | −3.62, 10.42 | −8.93, 4.66 | 0.67, 10.41 | 0.0258 |

As shown in Table 4, Stage IV patients treated with NEOD001 demonstrated a greater improvement in health status, as measured by 6MWD change in rank order from baseline to Month 9, relative to patients treated with placebo, compared to the difference seen with Stage I-III patients, with Stage IV patient having a change in rank order of +36.74 with p=0.0462 as compared to a change of −4.26 with p=0.6911 for Stage I-III patients.

TABLE 4

6MWD Change in Rank Order from Baseline to Month 9

|  |  | NEOD001 | Control | Difference | p-value |
|---|---|---|---|---|---|
| Stage I-III | N Month 9 | 92 | 91 | | |
|  | LSM (SE) | 139.16 (8.98) | 143.41 (8.91) | | |
|  | 95% CI | (121.44, 156.88) | (125.84, 160.99) | | |
|  | Change from Baseline | | | | |
|  | LSM (SE) | 5.05 (8.98) | 9.31 (8.91) | −4.26 (10.70) | |
|  | 95% CI | (−12.67, 22.77) | (−8.27, 26.89) | (−25.37, 16.85) | 0.6911 |
| Stage IV | N Month 9 | 38 | 39 | | |
|  | LSM (SE) | 165.89 (30.59) | 129.15 (29.79) | | |
|  | 95% CI | (104.89, 226.89) | (69.75, 188.55) | | |
|  | Change from Baseline | | | | |
|  | LSM (SE) | 43.95 (30.59) | 7.21 (29.79) | 36.74 (18.11) | |
|  | 95% CI | (−17.05, 104.95) | (−52.19, 66.62) | (0.64, 72.84) | 0.0462 |

Change from baseline in 6MWD was significantly greater at all time points through month 12 in the NEOD001+SOC group versus the placebo+SOC group. Mean (SD) duration of exposure was 389.4 (245.65) years in the NEOD001+SOC group and 352.7 (248.30) years in the placebo+SOC group. The mean (SD) number of infusions received was 14.5 (8.60) and 13.3 (8.71) in the NEOD001+SOC and placebo+SOC groups, respectively. Table 5 sets forth a summary of the VITAL Study results in Mayo Stage IV patients.

TABLE 5

Summary of VITAL Study results in Mayo Stage IV patients

| Outcome Measure | Hazard Ratio | Relative Risk Reduction | Change | p-value |
|---|---|---|---|---|
| Primary endpoint through 12 months* | 0.635 | 36.5% | n/a | 0.1409 |
| All-cause mortality through 12 months | 0.498 | 50.2% | n/a | 0.0556 |
| Cardiac mortality through 12 months | 0.378 | 62.2% | n/a | 0.0142 |
| SF-36 PCS to month 9 | n/a | n/a | +5.54 points | 0.0258 |
| 6MWD | n/a | n/a | +36.74 rank | 0.0462 |

*subjects who do not die are censored at the last date at which they were known to be alive, or 12 months, whichever comes first.

Example 5

Response of Patients with 6MWD of ≥150 Meters and EF of >50%

Figure 4A:
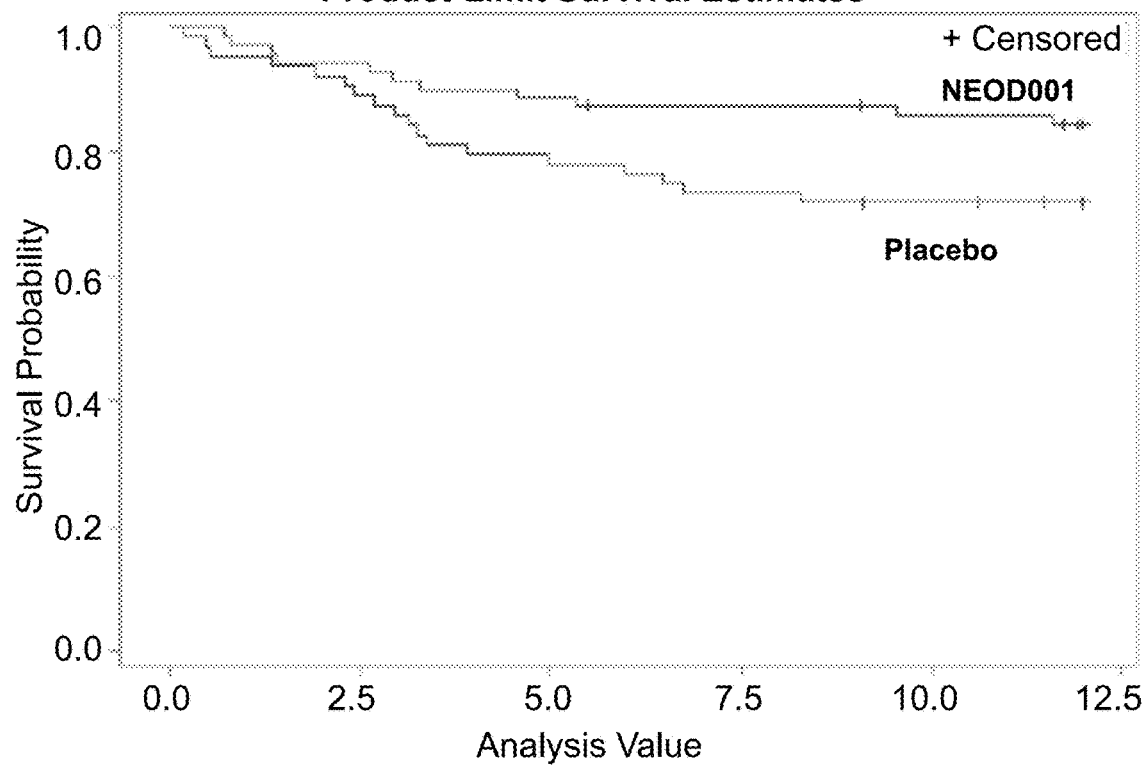
FIGS. 4A-4B show the all-cause mortality in AL amyloidosis patients with a baseline 6MWD≥150 meters and EF>50% that are treated with NEOD001 vs placebo for all Mayo Stages (FIG. 4A) and in Mayo Stage IV patients (FIG. 4B), respectively.
Figure 4B:
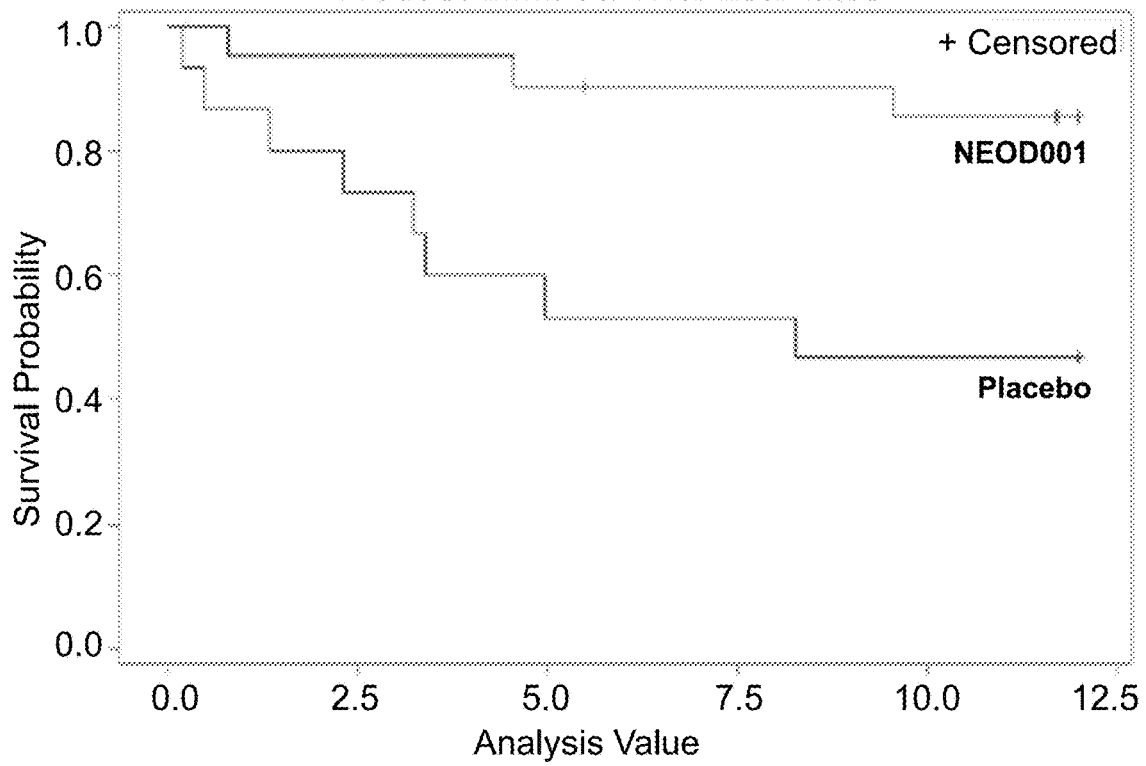

As shown in FIGS. 4A and 4B, patients with a baseline six minute walk distance (6MWD) of greater or equal to 150 meters and an ejection fraction (EF) of greater than 50% who were treated with NEOD001 demonstrated a greater improvement in health status, as measured by all-cause mortality through 12 months relative to patients treated with placebo. The results of patients of all Mayo stages having a baseline 6MWD≥150 meters and EF of >50% had an HR of 0.511 (48.9% relative risk reduction) with p=0.0741 and 95% CI (0.241, 1.083) (FIG. 4A). The results of Mayo Stage IV patients having a baseline 6MWD≥150 meters and EF of >50% had an HR of 0.201 (79.9% relative risk reduction) with p=0.0090 and 95% CI (0.053, 0.762) FIG. 4B. In addition, Mayo Stage IV patients having a bseline EF of >50% had an HR of 0.185 (81.5% relative risk reduction) with p=0.0049 and 95% CI (0.050, 0.689).

Overall, 257 patients in the safety population experienced 1 or more treatment-emergent AEs (TEAEs; see Table 6). The most common TEAEs (fatigue, nausea, peripheral edema, constipation, and diarrhea) were similar in both treatment arms, and both treatment arms had similar frequencies of serious TEAEs (NEOD001+SOC, 67.7%; placebo+SOC, 70.0%). Of the 288 serious AEs reported by 88 NEOD001-treated patients, the majority (95.5%) were considered not related to study drug, and TEAEs leading to death occurred more frequently in the placebo+SOC group (28 subjects, 21.5%) than in the NEOD001+SOC group (20 subjects, 15.4%). None of the deaths were considered to be related to study drug; cause of death in both groups was consistent with underlying disease and the known risk of cardiac complications. Overall safety results were similar within and across Mayo stages.

TABLE 6

Overall Summary of Treatment-Emergent Adverse Events (Safety Population)

| | NEOD001 + SOC (n = 130) | Placebo + SOC (n = 130) |
|---|---|---|
| TEAE by relationship[a] | | |
| Not related | 85 (65.4) | 81 (62.3) |
| Related | 42 (32.3) | 49 (37.7) |
| TEAE related with CTCAE grade ≥3 | 6 (4.6) | 11 (8.5) |
| TEAE leading to study drug withdrawal | 10 (7.7) | 16 (12.3) |
| TEAE leading to death | 20 (15.4) | 28 (21.5) |
| TEAE related leading to death | 0 | 0 |
| Serious TEAEs, n | 288 | 259 |
| Subjects reporting ≥1: | | |
| Serious TEAE | 88 (67.7) | 91 (70.0) |
| Serious TEAE by relationship[a] | | |
| Not related | 84 (64.6) | 86 (66.2) |
| Related | 4 (3.1) | 5 (3.8) |

Data reported as n (%) unless otherwise noted.
[a]Subjects reporting more than one adverse event are counted only once using the closest relationship to study drug, as assessed by the investigator.
CTCAE, common terminology criteria for adverse events; SOC, standard of care; TEAE, treatment-emergent adverse event.

Example 6

A Phase 3, Multicenter, Open-Label, Single-Arm, Efficacy and Safety Study of Birtamimab (NEOD001) Plus Standard of Care in Mayo Stage IV Subjects with Light Chain (AL) Amyloidosis The primary objective of the study (NEOD001-301) is to evaluate the efficacy of birtamimab plus standard of care when administered intravenously in Mayo Stage IV subjects with AL amyloidosis by assessing time to all-cause mortality. Secondary objectives are to evaluate birtamimab plus standard of care on the following: (1) change from baseline to month 9 in health related quality of life using the Short Form 36 questionnaire (SF-36v2), and (2) change from baseline to month 9 in the 6 Minute Walk Test (6MWT) distance (meters).

Newly diagnosed Mayo Stage IV subjects with AL amyloidosis receive birtamimab plus local standard of care chemotherapy. The initial first-line chemotherapy regimen must include bortezomib. Subjects remain on study until study completion, which occurs when approximately 16 primary endpoint events (all-cause mortality) have been reached or 62 subjects have completed 9 months of treatment. If the subject discontinues study drug prior to the end of the study, but is willing to continue to participate in study visits, the subject should have an Early Treatment Discontinuation (ETD) visit within 28-35 days after the last study drug administration and then have assessments every third month (see Table 8). All visits after the ETD Visit should occur on schedule, that is, at the time when the visit would have occurred had the subject remained on study drug.

Subject screening will occur during the 28 days prior to the first administration of study drug on Month 1-Day 1. The screening period may be extended upon approval by the Medical Monitor. Screening assessments are listed in Table 7, herein.

Two screening 6MWTs are required before the first administration of study drug. The first screening 6MWT is required to be performed between Days −28 and 5, at least 4 days prior to the second Screening 6MWT, which should be performed within 2 days prior to Month 1 Day 1. The postbaseline 6MWTs may be performed on the same day as study drug administration and must be completed prior to study drug infusion. If all eligibility requirements are met, Month 1-Day 1 assessments are completed, and treatment is initiated. Each visit is denoted by its "month" and "day" such that the first study drug infusion day is denoted as Month 1-Day 1; subsequent months use sequential numbers (e.g., the second dose is administered on Month 2-Day 1). "Cycle" is reserved to denote administration of chemotherapy. Assessment and visit windows are described in the Schedule of Events (Table 7). Each month, subjects receive their study drug infusion on Day 1 at the study site. For Months 1 through 3, subjects are assessed weekly, although not all visits are required to be at the study site. For Month 3 and all subsequent months until the end of the study, subjects are only required to return to the study site every 28 days for Day 1 dosing of study drug.

First-line chemotherapy must be a bortezomib-containing regimen, with bortezomib administered subcutaneously (SC), weekly. The first administration of chemotherapy, including bortezomib, is administered after Month 1 Day 1 study drug administration (following the post-study drug infusion observation period) such that Month 1-Day 1 of the study is equivalent to Cycle 1 Day 1 of chemotherapy. In addition to the visits outlined above, during the first cycle of chemotherapy, the subject must return to the study site for each weekly administration of bortezomib and for assessments prior to the administrations. During the second and third cycles of chemotherapy, bortezomib must be administered at the study site during the Month 2-Day 1, Month 2-Day 15, and Month 3-Day 1 visits (i.e., Cycle 2 Day 1, Cycle 2-Day 15, and Cycle 3-Day 1, respectively). If, for any reason in the opinion of the Investigator, the subject should continue to be seen weekly at the study site (e.g., toxicity that appears to exceed the anticipated side effects of the chemotherapy), then the other Cycle 2 and Cycle 3 weekly bortezomib administrations may be performed at the study site, as well. At the Investigator's discretion, if the subject is not experiencing any unanticipated or significant toxicity, the subject may be administered the Cycle 2-Days 8 and 22 and the Cycle 3 Days 8, 15 and 22 bortezomib by their local physician, rather than by the Investigator. Within 1 day prior to or on the day of each administration of bortezomib by the local physician, a healthcare professional must obtain pre-dose vital signs and central laboratory samples. However, if bortezomib is administered on a Monday (or there is an intervening holiday), then it is acceptable for the Homecare visit to take place on the previous Friday.

In the event that bortezomib doses are missed, the chemotherapy cycles may become misaligned with the monthly study drug dosing. In this case, the weekly visits during Months 1 through 3 should continue as described above in order to closely monitor subjects' health during the initial months of concomitant chemotherapy. Throughout the study, monthly doses of study drug should not be delayed or skipped due to adjustments that are made to chemotherapy dosing.

Safety and efficacy assessments are performed at each visit.

Inclusion Criteria (subjects must meet all of the following criteria):

1. Aged ≥18 years.
2. Newly diagnosed and AL amyloidosis treatment naïve.
3. Bone marrow demonstrating clonal plasma cells.
4. Confirmed diagnosis of AL amyloidosis by the following:
    Histochemical diagnosis of amyloidosis determined by polarizing light microscopy of green birefringent material in Congo red-stained tissue specimens OR characteristic electron microscopy appearance, AND
    Confirmatory immunohistochemistry OR mass spectroscopy of AL amyloidosis.
5. Confirmed diagnosis of AL amyloidosis by mass spectrometry or immunoelectron microscopy of amyloid material in tissue biopsy if the subject meets any of the following:
    Is black or African American.
    Is over 75 years of age with concurrent monoclonal gammopathy.
    Has a history of familial amyloidosis and has concurrent monoclonal gammopathy.
    OR
    If the subject meets any of the above 3 conditions and has echocardiographic evidence of amyloidosis, biopsy-proven amyloidosis with a monoclonal gammopathy and no tissue is available for mass spectrometry or immunoelectron microscopy, the subject must have gene sequencing consistent with transthyretin (TTR) wild type (e.g., no TTR mutation present) AND must score 0 in technetium-99m-3,3-diphosphono-1,2 propanodicarboxylic acid (99mTc DPD; Rapezzi 2011), hydroxymethylenediphosphonate (99mTc HMDP; Galat 2015), or pyrophosphate (99mTc PYP; Bokhari 2013) scintigraphy.
6. Cardiac involvement as defined by all of the following:
    Past documented or presently noted clinical signs and symptoms supportive of a diagnosis of heart failure in the setting of a confirmed diagnosis of AL amyloidosis in the absence of an alternative explanation for heart failure.
    Either an endomyocardial biopsy demonstrating AL amyloidosis or an echocardiogram demonstrating a mean left ventricular wall thickness at diastole >12 mm in the absence of other causes (e.g., severe hypertension, aortic stenosis), which would adequately explain the degree of wall thickening.
7. Confirmed Mayo Stage IV as defined by:
    NT-proBNP≥1800 pg/mL, and
    Troponin-T>0.03 ng/mL, and
    dFLC≥18 mg/dL.
8. Planned first-line chemotherapy contains bortezomib administered subcutaneously (SC) weekly.
9. Adequate bone marrow reserve, hepatic function, and renal function, as demonstrated by:
    Absolute neutrophil count (ANC)≥1.0×109/L.
    Platelet count≥75×109/L.
    Hemoglobin≥9 g/dL.
    Total bilirubin≤2 times the upper limit of normal (×ULN).
    Aspartate aminotransferase (AST)/serum glutamic oxaloacetic transaminase (SGOT)≤3×ULN.
    Alanine aminotransferase (ALT)/serum glutamic pyruvic transaminase (SGPT)≤3×ULN.
    Alkaline phosphatase (ALP)≤5×ULN (except for subjects with hepatomegaly and isozymes specific to liver, rather than bone).
    Estimated glomerular filtration rate (eGFR)≥30 mL/min/1.73 m2 as estimated by the Chronic Kidney Disease Epidemiology Collaboration (CKD-EPI) equation.

10. Seated systolic blood pressure 90-180 mmHg.
11. Distance walked during each Screening 6MWT is ≥30 meters and ≤550 meters.
12. Women of childbearing potential (WOCBP) must have two negative pregnancy tests during Screening, the second within 24 hours prior to the first administration of study drug, and must agree to use highly effective physician-approved contraception from Screening to 90 days following the last study drug administration.
13. Male subjects must be surgically sterile or must agree to use highly effective physician-approved contraception from Screening to 90 days following the last study drug administration.
14. Ability to understand and willingness to sign an informed consent form prior to initiation of any study procedures.

Exclusion Criteria (subjects must meet none of the following criteria):
1. Non-AL amyloidosis.
2. NT-proBNP>8,500 pg/mL.
3. Meets the International Myeloma Working Group (IMWG) definition of Multiple Myeloma.
   Note that subjects who meet the IMWG definition of symptomatic multiple myeloma with signs and/or symptoms attributable only to associated amyloidosis are potentially eligible upon approval of the Sponsor.
4. Subject is eligible for and plans to undergo ASCT or organ transplant during the study.
5. Symptomatic orthostatic hypotension that in the medical judgment of the Investigator would interfere with subject's ability to safely receive treatment or complete study assessments.
6. Myocardial infarction, uncontrolled angina, severe uncontrolled ventricular arrhythmias, or electrocardiographic (ECG) evidence of acute ischemia, within 6 months prior to the Month 1-Day 1 Visit.
7. Severe valvular stenosis (e.g. aortic or mitral stenosis with a valve area<1.0 cm2) or severe congenital heart disease.
8. ECG evidence of acute ischemia or active conduction system abnormalities with the exception of any of the following:
   First degree AV-block.
   Second degree AV-block Type 1 (Mobitz Type 1/Wenckebach type).
   Right or left bundle branch block.
   Atrial fibrillation with a controlled ventricular rate (uncontrolled [>110 bpm] ventricular rate is not allowed [determined by an average of three beats in Lead II or three representative beats if Lead II is not representative of the overall EKG]).
9. Peripheral neuropathy assessed as National Cancer Institute-Common Terminology Criteria for Adverse Events (NCI-CTCAE) Grade 2 with pain, Grade 3, or Grade 4.
10. Subject is receiving oral or IV antibiotics, antifungals or antivirals within 1 week of Month 1-Day 1 with the exception of prophylactic oral agents.
11. Prior treatment with hematopoietic growth factors, transfusions of blood or blood products within 1 week of Month 1-Day 1.
12. Prior radiotherapy within 4 weeks of Month 1-Day 1.
13. Major surgery within 4 weeks of Month 1-Day 1 or planned major surgery during the study.
14. Active malignancy with the exception of any of the following:
   Adequately treated basal cell carcinoma, squamous cell carcinoma, or in situ cervical cancer.
   Adequately treated Stage I cancer from which the subject is currently in remission and has been in remission for 2 years.
   Low-risk prostate cancer with Gleason score<7 and prostate-specific antigen<10 mg/mL.
   other cancer from which the subject has been disease-free for ≥2 years.
15. History of severe allergy to any of the components of birtamimab such as histidine/L histidine hydrochloride monohydrate, trehalose dehydrate, or polysorbate 20 or history of Grade >3 infusion-related AEs or hypersensitivity to another monoclonal antibody, or known hypersensitivity to diphenhydramine (or an equivalent H1 antihistamine) or acetaminophen (or its equivalent, paracetamol).
16. Known or history of uncontrolled, active HIV, hepatitis B or hepatitis C infection.
17. Prior treatment with plasma cell-directed chemotherapy, birtamimab, daratumumab, 11-1F4, anti-serum amyloid P antibody, doxycycline for amyloid, or other investigational treatment directed at amyloid.
18. Treatment with another investigational agent within 30 days of Month 1-Day 1.
19. Women who are pregnant or lactating.
20. Any condition which could interfere with, or the treatment for which might interfere with, the conduct of the study or which would, in the opinion of the Investigator, unacceptably increase the subject's risk by participating in the study.
21. Subject is under legal custodianship.
22. History of epilepsy or seizure disorder with the exception of childhood febrile seizures.
23. Waldenstrom's macroglobulinemia and/or immunoglobulin M (IgM) monoclonal gammopathy.

Study Drug: Study drug consists of birtamimab (24 mg/kg) supplied as a sterile, lyophilized dosage form in a 20/25 mL vial containing 500 mg birtamimab. Each vial is reconstituted with 9.6 mL sterile water for injection (WFI) to a concentration of 50 mg/mL resulting in a buffered, isotonic, preservative-free solution. Study drug is administered once every 28 days as an initial 120 (±10)-minute IV infusion. If the subject tolerates the initial infusion, subsequent infusions may be administered over 60 (±10) minutes. The length of the infusion may be extended over a longer period of time if and when it is clinically indicated. A minimum of 21 days between doses is required.

Premedication: All subjects are premedicated for each dose of study drug with 25 mg diphenhydramine (or an equivalent dose of a H1 antihistamine) and 650 mg acetaminophen (or an equivalent paracetamol dose) within 30-90 minutes prior to study drug administration.

Standard of Care Chemotherapy: All subjects receive concomitant standard of care chemotherapy, which must include bortezomib administered subcutaneously on a weekly basis for the initial, first-line chemotherapy regimen. Subsequent chemotherapy regimens may be prescribed as per standard of care at the Investigator's discretion. Antiviral prophylaxis is required.

Statistical Considerations

Analysis Populations. The Intent-to-Treat (ITT) Population includes all subjects with Mayo Stage IV AL amyloidosis who receive any amount of study drug. The ITT Population is the primary population used for efficacy and safety analyses.

Efficacy Analyses. Primary Analysis—The primary endpoint is time to all-cause mortality. For all-cause mortality, all deaths occurring after the first infusion of study drug (Study Day 1) through the study's last subject last visit (LSLV) are included. Using an exponential survival model, the estimated survival percentage at 9 months is estimated. Using an exact binomial test, the estimated survival percentage is compared to the historical control value of 49%.

Key Secondary Efficacy Analyses—If the primary analysis concludes in favor of birtamimab, then the data for the placebo plus SOC Mayo Stage IV subjects from Study NEOD001 CL0002 [VITAL] is used to compare: (1) Change from baseline to Month 9 in the PCS score of the SF-36v2, and/or (2) Change from baseline to Month 9 in the 6MWT distance (meters). For both of these variables, change from baseline to Month 9 and 95% confidence intervals are computed. If the lower bounds of the confidence intervals are greater than the observed values from the placebo group in VITAL, then the study concludes that that birtamimab is superior to control.

TABLE 7

Schedule of Events

| Assessments | Screening[1] Day −28 to Day −1 | Day −2 or Day −1 | Month 1 Day 1 | Month 1 Days 8, 15, 22 (±2) | Month 2 Day 1 | Month 2 Days 8[2], 15, 22[2] (±2) | Month 3 Day 1 | Month 3 Days 8[2], 15[2], 22[2] (±2) | Months 6, 9, 12, etc. (Every 3rd Month) Day 1 (±5) | All Other Months Day 1 (±5) | EOT/ETD[3] |
|---|---|---|---|---|---|---|---|---|---|---|---|
| Written Informed Consent | X | | | | | | | | | | |
| Eligibility Review | X | | | | | | | | | | |
| Medical History[4] | X | | | | | | | | | | |
| Confirmation of AL Amyloidosis[5] | X | | | | | | | | | | |
| SF-36v2 Health Survey[6] | | X | | | X | | X | | X | | X |
| Echocardiogram | X[7] | | | | | | | | Every 6th mo[7] | | X[7] |
| 12-lead Triplicate ECG[8] | X | | X | | X | | X | | X | | X |
| Complete PE[9] | X | | | | | | | | | | X |
| Symptom-Directed PE[10] | | X | | | X | | X | | X | X | |
| NYHA Class | X | X | | | X | | X | | X | X | X |
| Local Laboratory | | | | | | | | | | | |
| Hematology & Chemistry[11] | | | | X | X | X[12] | X | X[12] | X | X | |
| Serum/Urine Pregnancy (WOCBP) | | | X[13] | | X[14] | | X[14] | | X[14] | X[14] | X[15] |
| Central Laboratory[16] | | | | | | | | | | | |
| Hematology & Chemistry | X | X | | X | X | X | X | X | X | X | X |
| Amylase | X | X | | | X | | X | | X | X | X |
| Coagulation[17] | | X | | | X | | X | | X | X | X |
| Complements C$_3$, C$_4$ | | X | | | X | | X | | X | | X |
| Troponin T | X | X | | | X | | X | | X | X | X |
| NT-proBNP[18] | X | X | | | X | | X | | X | X | X |
| Tryptase | | X | | | | | | | | | |
| Serum Free Light Chains (sFLCs) | X | X | | | X | | X | | X | X | X |
| Serum Pregnancy (WOCBP) | X | | | | | | | | | | X |
| Urinalysis | X | X | | | X | | X | | X | X | X |
| 6-Minute Walk Test (6MWT)[19] | X[20] | X[20] | | | | | X | | X | | X |
| Bioanalytical Laboratory | | | | | | | | | | | |
| Anti-birtamimab Antibody Sample (pre-dose) | | | X | | X | | X | | X | X | X |
| Archive Sample (pre-dose)[21] | | | X | | X | | X | | X | X | |
| Premedication Administration[22] | | | X | | X | | X | | X | X | |
| Vital Signs[23] | X | | X | X | X | X | X | X | X | X | X |
| Study Drug Infusion[24] | | | X | | X | | X | | X | X | |
| Chemotherapy & Antiviral Prophylaxis[25] | | | X[26] | X[26] | X[26] | X[26,27] | X[26] | X[27] | X[26] | X[26] | |
| Adverse Event Assessment | X | X | X | X | X | X[12] | X | X[12] | X | X | X[28] |
| Concomitant Medications | X | X | X | X | X | X[12] | X | X[12] | X | X | X |
| Vital Status Assessment | | | | | | | | | | | X[29] |

BP = blood pressure;
ECG = electrocardiogram;
EOI = end of infusion;
EOT = End of Treatment;
ETD = Early Treatment Discontinuation;
HR = heart rate;
NT proBNP = N terminal pro-brain natriuretic peptide;
NYHA = New York Heart Association;
PE = physical exam;
RR = respiratory rate;
SC = subcutaneous;
6MWT = 6-minute walk test;
SF 36v2 = Short Form-36 Version 2;
ULN = upper limit of normal;
WOCBP = women of childbearing potential.

Table 7 Footnotes
1. The 28-day Screening period may be extended upon approval by the Medical Monitor. Individual test results that do not meet eligibility requirements may be repeated, with the exception of 6MWT; full rescreening is allowed once per subject.
2. Cycle 2-Days 8 and 22 and Cycle 3-Days 8, 15 and 22 bortezomib-containing chemotherapy should be administered by the Investigator at the study site if subject had significant toxicity; otherwise, it may be administered by local physician at Investigator's discretion.
3. EOT/ETD Visit to occur 28-35 days after the last study drug administration.
4. Obtain comprehensive cardiac, hematologic, and oncologic medical history; additionally, for all other conditions obtain relevant medical history for the past 5 years (including all major hospitalizations and surgeries), as well as the subject's current medical status.
5. Results from mass spectrometry tissue typing, immunoelectron microscopy, gene sequencing, and/or 99mTc scintigraphy must be obtained prior to randomization to assess eligibility for subjects identified in Inclusion Criterion #5.
6. At visits where the SF-36v2 (Appendix 4) is to be administered, the SF-36v2 needs to be administered prior to the performance of any other study assessments on that day.
7. If an echocardiogram has been conducted within 90 days prior to Screening Day −28, it does not need to be repeated during Screening and the previous result can be used for eligibility. After Screening, perform echocardiograms every 6 months within 10 days prior to Day 1; repeat at EOT/ETD if not performed within 60 days prior to visit. To be eligible for the additional cardiac imaging analysis, the subject must have had a 4-chamber view, 2-dimensional echocardiogram with Doppler.
8. ECG to be performed in triplicate as follows: Month 1-Day 1: within 30 minutes before dosing and 1 hour (±15 min) post-EOI; All Other Visits (Months 1, 2, 3 and every 3 months starting at Month 6): within 30 minutes before dosing or any time on non-infusion days. Medications given for prophylaxis chemotherapy-induced side effects should not be administered prior to completion of the postinfusion ECG.
9. Complete PE includes height (Screening only), weight, and examination of the following: general appearance; head, ears, eyes, nose, and throat; neck; skin; cardiovascular system; respiratory system; gastrointestinal system; and nervous system. Assess macroglossia, submandibular nodes/fullness, adenopathy, ecchymoses, liver/spleen size (palpable +/−), ascites (+/−), and edema (which should be quantified on a scale of 0-4).
10. Symptom-directed PE should be as clinically indicated and also include weight, and assessment of macroglossia, submandibular nodes/fullness, adenopathy, ecchymoses, liver/spleen size (palpable +/−), ascites (+/−), and edema (which should be quantified on a scale of 0-4).
11. Local laboratory results for hematology and chemistry will be used for subject management and should be reviewed for safety assessment prior to administration of chemotherapy but will not be collected in the electronic case report forms or the clinical database.
12. Perform only if subject returns to study site for this visit.
13. Use local lab for serum pregnancy test within 24 hours prior to Month 1-Day 1 study drug administration.
14. Obtain local urine pregnancy test prior to study drug administration.
15. Obtain local laboratory serum pregnancy test 90 (±5) days after the last study drug administration.
16. Collect central laboratory samples before 6MWT, if being performed on the same day.
17. Collect PT/INR and PTT at each time point.
18. NT-proBNP should be drawn before conducting 6MWT if being performed on the same calendar day.
19. Subjects should plan to be able to return to the same clinical site for each 6MWT from first Screening through Month 9. The postbaseline 6MWT may be administered on the same calendar day that study drug is administered (i.e., Months 3, 6, 9, etc.) as long as the NT-proBNP sample is drawn before conducting the 6MWT and the 6MWT is completed before initiation of the study drug infusion. Collect BP and HR pre- and post-6MWT administration.
20. The first Screening 6MWT must be performed between Days −28 and −5, at least 4 days prior to the second Screening 6MWT, which should be performed within 2 days prior to the Month 1-Day 1 visit (i.e., on Day −2 or Day −1).
21. Archive serum samples will only be collected from those subjects who have consented to the collection and archiving of their samples for future correlative testing.
22. All subjects are to receive 25 mg diphenhydramine (or an equivalent dose of a H1 antihistamine) and 650 mg acetaminophen (or an equivalent paracetamol dose) within 30 90 minutes prior to the start of infusion.
23. Vital signs include BP, HR, RR, and temperature; assess in same position for all time points after the subject has been at rest for >5 minutes. Pre-dose assessments should be performed after administration of premedication. Screening and non-infusion days: any time; Month 1-Day 1: Within 30 minutes before dosing, halfway through infusion (i.e., approximately 60 minutes after the start of the infusion), immediately at EOI (+10 min), 0.5 hour (±10 min) post-EOI, and 1 hour (±10 min) post-EOI. All Other Months-Day 1: Within 30 minutes before dosing, EOI (+10 min), and 1 hour (±10 min) post-EOI.
24. Subjects should be closely monitored for 90 (±10) minutes following completion of the study drug infusion. The Investigator may increase this standard monitoring time if deemed appropriate or per local standards. In the event of any clinical concerns or suspicious signs or symptoms after the infusion, the subject will remain under observation for as long as the Investigator deems it appropriate.
25. First-line chemotherapy must be a bortezomib-containing regimen, with bortezomib administered weekly, SC, according to the approved prescribing information and local institutional practices. Antiviral prophylaxis is required. When chemotherapy is administered on same day as study drug, the chemotherapy must be administered AFTER the post-study drug infusion observation period. Number of first-line chemotherapy cycles and subsequent chemotherapy regimens will be administered per standard of care at the Investigator's discretion.
26. Bortezomib must be administered at the study site for Cycle 1-Days 1, 8, 15, and 22; Cycle 2-Days 1 and 15; and on Day 1 of subsequent cycles, after review of local labs, study drug administration, and the post-study drug infusion observation period.

27. Cycle 2-Days 8 and 22, and Cycle 3-Days 8, 15, and 22 chemotherapy may be administered by local physician with a Homecare visit by a Prothena-sponsored healthcare professional to the subject within 1 day prior to or pre-dose on the day of each bortezomib administration to obtain vital signs, blood samples for central laboratory testing, and bioanalytical samples (if applicable). If bortezomib is administered on a Monday, the Homecare visit may occur on the previous Friday. If significant toxicity occurs during Cycle 1, subject should return to the study site for Cycle 2 and Cycle 3 visits until Investigator deems it appropriate for local administration.

28. New SAEs occurring beyond the EOT/ETD Visit or >28 days after the last administration of study drug, whichever is later, will be reported to the Sponsor or its designee only if, in the judgement of the Investigator, the SAE is associated with any protocol intervention (i.e., related to study procedure or previous study drug exposure).

29. For all subjects who received a dose of study drug: Conduct vital status assessment approximately 3 months after the subject's last visit and approximately every 3 months thereafter.

TABLE 8

Schedule of Events For Subjects Who Discontinue Study Drug Early but Agree to Return For Assessments After the ETD Visit

| Assessments | Months 3, 6, 9, 12 Day 1 (±5)[1] | Every Third Month After Month 12[2] (e.g., Months 15, 18, 21) Day 1 (±5) | Every 3 Months after Last Visit |
|---|---|---|---|
| SF-36v2 Health Survey[3] | X | | |
| Echocardiogram | Months 6 and 12[4] | | |
| 12-lead Triplicate ECG[5] | X | | |
| Symptom-Directed PE[6] | X | | |
| NYHA Class | X | | |
| *Local Laboratory* | | | |
| Serum Pregnancy (WOCBP) | X[7] | | |
| *Central Laboratory[8]* | | | |
| Hematology & Chemistry | X | | |
| Amylase | X | | |
| Coagulation[9] | X | | |
| Complements $C_3$, $C_4$ | X | | |
| Troponin T | X | | |
| NT-proBNP | X | | |
| Serum Free Light Chains (sFLCs) | X | | |
| Urinalysis | X | | |
| 6-Minute Walk Test (6MWT) | X | X[10] | |
| *Bioanalytical Laboratory* | | | |
| Anti-NEOD001 Antibody Sample[11] | X | | |
| Vital Signs | X[12] | X[10] | |
| Adverse Event Assessment | X[13] | X[10,13] | |
| Concomitant Medications | X | X[10] | |
| Health Status & Hospitalizations | X[14] | X[10,14] | X[10,13,14] |
| Vital Status Assessment | | | X[15] |

BP = blood pressure; ECG = electrocardiogram; ETD = Early Treatment Discontinuation; HR = heart rate; NT proBNP = N terminal pro-brain natriuretic peptide; NYHA = New York Heart Association; PE = physical exam; RR = respiratory rate; 6MWT = 6-minute walk test; SF 36v2 = Short Form-36 Version 2; WOCBP = women of childbearing potential.

Table 8 Footnotes

[1] If a subject discontinues study drug prior to the end of the study, but is willing to continue to participate in study visits, the subject should have an ETD Visit within 28-35 days after the last study drug administration and then have assessments performed every third month (i.e., Months 3, 6, 9, and 12, or whatever remains of these visits). All visits after the ETD Visit should occur on schedule, that is, at the time when the visit would have occurred had the subject remained on study drug.

[2] If subject is willing to return to the study site, otherwise, subjects will receive vital status.

[3] Administer SF-36v2 prior to the performance of any other study assessments on the day it is administered.

[4] Perform echocardiograms within 10 days prior to Day 1 of Months 6 and 12.

[5] ECG to be performed in triplicate.

[6] Symptom-directed PE should be as clinically indicated and also include weight, and assessment of macroglossia, submandibular nodes/fullness, adenopathy, ecchymoses, liver/spleen size (palpable +/−), ascites (+/−), and edema (which should be quantified on a scale of 0-4).

[7] Obtain local laboratory serum pregnancy test 90 (±5) days after the last study drug administration.

[8] Collect central laboratory samples before 6MWT, if being performed on the same day.

[9] Collect PT/INF and PTT at each time point.

[10] After Month 12, if the subject is willing to return to the study site, perform or collect the following every third month (e.g., Months 15, 18, 21): 6MWT (which includes BP and HR pre- and post-6MWT administration), adverse events, concomitant medications, overall health status, as well as details of any hospitalizations.

[11] Collect if an earlier sample established the presence of anti-NEOD001 antibodies or if a subject discontinued treatment due to a suspected immunologic reaction.

[12] Collect BP, HR, RR, and temperature any time during visit.

TABLE 8-continued

Schedule of Events For Subjects Who Discontinue Study Drug Early but Agree to Return For Assessments After the ETD Visit

| Assessments | Months 3, 6, 9, 12 Day 1 (±5)[1] | Every Third Month After Month 122 (e.g., Months 15, 18, 21) Day 1 (±5) | Every 3 Months after Last Visit |
|---|---|---|---|

[13]New SAEs occurring beyond the EOT/ETD Visit or /days after the last administration of study drug, whichever is later, will be reported to the Sponsor or its designee only if, in the judgement of the Investigator, the SAE is associated with any protocol intervention (i.e., related to study procedure or previous study drug exposure).
[14]All hospitalizations and deaths occurring during this period need to be reported to the Sponsor or its designee.
[15]Conduct a vital status assessment approximately 3 months after the subject's last visit and approximately every 3 months thereafter.

The disclosure of every patent, patent application, and publication cited herein is hereby incorporated herein by reference in its entirety. While this invention has been disclosed with reference to specific embodiments, other embodiments and variations of this disclosure can be devised by others skilled in the art without departing from the true spirit and scope of the disclosure. The appended claims include all such embodiments and equivalent variations.

```
SEQUENCES
Humanized antibody sequence containing murine and human residues
(humanized 2A4 light chain variable region version 3)
                                                         SEQ ID NO: 01
DVVMTQSPLSLPVTPGEPASISCRSSQSLVHSTGNTYLHWYLQKPGQSPQLLIYKVSNRFSGVPDRFSGSGSGTD

FTLKISRVEAEDVGVYYCSQSTHVPFTFGGGTKVEIK

Humanized antibody sequence containing murine and human residues
(humanized 2A4 heavy chain variable region version 3)
                                                         SEQ ID NO: 02
EVQLVESGGGLVQPGGSLRLSCAASGFTFNTYAMYWIRQAPGKGLEWVARIRSKSNNYAIYYADSVKDRFTISRD

DSKNSLYLQMNSLKTEDTAVYYCARPYSDSFAYWGQGTLVTVSS

2A4 VL CDR1
                                                         SEQ ID NO: 03
RSSQSLVHSTGNTYLH

2A4 VL CDR2
                                                         SEQ ID NO: 04
KVSNRFS

2A4 VL CDR3
                                                         SEQ ID NO: 05
SQSTHVPFT

2A4 VH CDR1
                                                         SEQ ID NO: 06
GFTFNTYAMY

2A4 VH CDR2
                                                         SEQ ID NO: 07
RIRSKSNNYAIYYADSVKD

2A4 VH CDR3
                                                         SEQ ID NO: 08
PYSDSFAY

7D8 VL CDR1
                                                         SEQ ID NO: 09
RSSLSLVHSTGNTYLH
```

-continued

Humanized antibody sequence containing murine and human residues
(humanized 2A4 kappa light chain)
SEQ ID NO: 10
DVVMTQSPLSLPVTPGEPASISCRSSQSLVHSTGNTYLHWYLQKPGQSPQLLIYKVSNRFSGVPDRFSGSGSGTD

FTLKISRVEAEDVGVYYCSQSTHVPFTFGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYACEVTHQGLSSPVTKSFNRGEC

Humanized antibody sequence containing murine and human residues
(humanized 2A4 IgG1 heavy chain variant 1 (G1m1 allotype))
SEQ ID NO: 11
EVQLVESGGGLVQPGGSLRLSCAASGFTFNTYAMYWIRQAPGKGLEWVARIRSKSNNYAIYYADSVKDRFTISRD

DSKNSLYLQMNSLKTEDTAVYYCARPYSDSFAYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTYICNVNHKPSNTKVDKRVEPKSCDKT

HTCPPCPAPELLGGPSVFLFPPKPKDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVYTLPPSRDELTKNQVSLTCLVKGFY

PSDIAVEWESNGQPENNYKTTPPVLDSDGSFFLYSKLTVDKSRWQQGNVFSCSVMHEALHNHYTQKSLSLSPGK

Humanized antibody sequence containing murine and human residues
(humanized 2A4 IgG1 heavy chain variant 2 (G1m3 allotype))
SEQ ID NO: 12
EVQLVESGGGLVQPGGSLRLSCAASGFTFNTYAMYWIRQAPGKGLEWVARIRSKSNNYAIYYADSVKDRFTISRD

DSKNSLYLQMNSLKTEDTAVYYCARPYSDSFAYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTYICNVNHKPSNTKVDKRVEPKSCDKT

HTCPPCPAPELLGGPSVFLFPPKPKDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVYTLPPSREEMTKNQVSLTCLVKGFY

PSDIAVEWESNGQPENNYKTTPPVLDSDGSFFLYSKLTVDKSRWQQGNVFSCSVMHEALHNHYTQKSLSLSPGK

Humanized antibody sequence containing murine and human residues
(humanized 2A4 IgG2 heavy chain)
SEQ ID NO: 13
EVQLVESGGGLVQPGGSLRLSCAASGFTFNTYAMYWIRQAPGKGLEWVARIRSKSNNYAIYYADSVKDRFTISRD

DSKNSLYLQMNSLKTEDTAVYYCARPYSDSFAYWGQGTLVTVSSASTKGPSVFPLAPCSRSTSESTAALGCLVKD

YFPEPVTVSWNSGALTSGVHTFPAVLQSSGLYSLSSVVTVPSSNFGTQTYTCNVDHKPSNTKVDKTVERKCCVEC

PPCPAPPVAGPSVFLFPPKPKDTLMISRTPEVTCVVVDVSHEDPEVQFNWYVDGVEVHNAKTKPREEQFNSTFRV

VSVLTVVHQDWLNGKEYKCKVSNKGLPAPIEKTISKTKGQPREPQVYTLPPSREEMTKNQVSLTCLVKGFYPSDI

AVEWESNGQPENNYKTTPPMLDSDGSFFLYSKLTVDKSRWQQGNVFSCSVMHEALHNHYTQKSLSLSPGK 11-1F4 monoclonal antibody variable light [kappa]
SEQ ID NO: 14
DVVMTQTPLSLPVSLGDQASISCRSSQSLVHRNGNTYLHWYLQKPGQSPKLLIYKVSNRFSGVPDRFSGSGSGTD

FTLKISRVEAEDLGLYFCFQTTYVPNTFGGGTKLEIK 11-1F4 monoclonal antibody variable heavy
SEQ ID NO: 15
QVQLKESGPGLVAPSQSLSITCTVSGFSLSSYGVSWVRQPPGKGLEWLGVIWGDGSTNYKPNLMSRLSISKDISK

SQVLFKLNSLQTDDTATYYCVTLDYWGQGTSVTVSS 11-1F4 monoclonal antibody CDR1 light chain
SEQ ID NO: 16
RSSQSLVHRNGNYTLH 11-1F4 monoclonal antibody CDR2 light chain
SEQ ID NO: 17
LVSNRFS 11-1F4 monoclonal antibody CDR3 light chain
SEQ ID NO: 18
FNTTYVPNT -continued 11-1F4 monoclonal antibody CDR1 heavy chain
SEQ ID NO: 19
SYGVSW 11-1F4 monoclonal antibody CDR2 heavy chain
SEQ ID NO: 20
VIWGDGSTNYHPNLMSRLSIS 11-1F4 monoclonal antibody CDR3 heavy chain
SEQ ID NO: 21
LDY 11-1F4 monoclonal antibody variable light /kappa/
SEQ ID NO: 22

```
gatgttgtga tgacccaaac tccactctcc ctgcctgtca gtcttggaga tcaagcctcc    60
atctcttgca gatctagtca gagccttgta catagaaatg gaaacaccta tttacattgg   120
tacctgcaga agccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tttgggactt tatttctgtt ttcaaactac atatgttccg   300
aacacgttcg aggggggac caagctggaa ataaaa                              336
```

11-1F4 monoclonal antibody variable heavy
SEQ ID NO: 23

```
caggtgcagc tgaaggagtc aggacctggc ctggtggcgc cctcacagag cctgtccatc    60
acatgcactg tctcagggtt ctcattaagc agctatggtg taagctgggt tcgccagcct   120
ccaggaaagg gtctggagtg gctgggagta atatgggtg acgggagcac aaattatcat   180
ccaaatctca tgtccagact gagtatcagc aaggatattt ccaagagcca agttctcttc   240
aaactgaata gtctgcaaac tgatgacaca gccacgtact actgtgtcac cttcgactac   300
tggggtcaag gaacctcagt caccgtctcc tca                                 333
```

What is claimed is:

1. A method of treating a patient having AL amyloidosis, comprising:
   (a) determining:
      (i) the Mayo Stage of the patient's AL amyloidosis;
      (ii) the 6 minute walk distance (6MWD) and ejection fraction (EF) of the patient;
      (iii) the Mayo Stage of the patient's AL amyloidosis and the EF of the patient; or
      (iv) the Mayo Stage of the patient's AL amyloidosis, and the 6MWD and the EF of the patient; and
   (b) selecting the patient for treatment with an antibody comprising a light chain variable region comprising three complementarity determining regions set forth as SEQ ID NOs: 3, 4 and 5, and a heavy chain variable region comprising three complementarity determining regions set forth as SEQ ID NOs: 6, 7 and 8 if the patient:
      (i) has Mayo Stage IV AL amyloidosis;
      (ii) has a 6MWD≥150 meters and an EF>50% at baseline;
      (iii) has Mayo Stage IV AL amyloidosis and EF>50% at baseline; or
      (iv) has Mayo Stage IV AL amyloidosis, a 6MWD≥150 meters and an EF>50% at baseline; and
   (c) administering an effective dosage of the antibody to the selected patient.

2. The method of claim 1, wherein the selected patient has Mayo Stage IV AL amyloidosis.

3. The method of claim 1, wherein the selected patient has a 6MWD≥150 meters and an EF>50%.

4. The method of claim 2, wherein the selected patient has an EF>50%.

5. The method of claim 4, wherein the selected patient has a 6MWD≥150 meters.

6. The method of claim 1, wherein the antibody is a humanized antibody.

7. The method of claim 1, wherein the light chain variable region comprises the amino acid sequence set forth as SEQ ID NO: 1.

8. The method of claim 1, wherein the heavy chain variable region comprises the amino acid sequence set forth as SEQ ID NO: 2.

9. The method of claim 1, wherein the light chain variable region comprises the amino acid sequence set forth as SEQ ID NO: 1, and the heavy chain variable region comprises the amino acid sequence set forth as SEQ ID NO: 2.

10. The method of claim 1, wherein the antibody is birtamimab.

11. The method of claim 1, wherein the selected patient is newly diagnosed and AL amyloidosis treatment naïve.

12. The method of claim 1, wherein the selected patient previously received or concomitantly receives administration of melphalan, prednisone, dexamethasone, bortezomib, cyclophosphamide, lenalidomide, doxorubicin, doxycycline, daratumumab, autologous transplant, or a combination thereof.

13. The method of claim 1, wherein the selected patient previously received or concomitantly receives administration of Cyclophosphamide, Bortezomib and Dexamethasone (CyBorD).

14. A method of treating a patient having AL amyloidosis, comprising:
   (a) selecting a patient having AL amyloidosis for treatment with an antibody comprising a light chain variable region comprising three complementarity determining regions set forth as SEQ ID NOs: 3, 4 and 5, and a heavy chain variable region comprising three complementarity determining regions set forth as SEQ ID NOs: 6, 7 and 8 if the patient has:
      (i) Mayo Stage IV AL amyloidosis;
      (ii) a 6 minute walk distance (6MWD)≥150 meters and EF>50% at baseline;
      (iii) Mayo Stage IV AL amyloidosis and an EF>50% at baseline; or
      (iv) Mayo Stage IV AL amyloidosis and a 6MWD≥150 meters and EF>50% at baseline; and
   (b) administering an effective dosage of the antibody to the selected patient.

15. The method of claim 14, wherein the selected patient has Mayo Stage IV AL amyloidosis.

16. The method of claim 14, wherein the selected patient has a 6MWD≥150 meters and an EF>50%.

17. The method of claim 15, wherein the selected patient has a 6MWD≥150 meters and an EF>50%.

18. The method of claim 15, wherein the selected patient has an EF>50%.

19. The method of claim 14, wherein the antibody is a humanized antibody.

20. The method of claim 14, wherein the light chain variable region comprises the amino acid sequence set forth as SEQ ID NO: 1.

21. The method of claim 14, wherein the heavy chain variable region comprises the amino acid sequence set forth as SEQ ID NO: 2.

22. The method of claim 14, wherein the light chain variable region comprises the amino acid sequence set forth as SEQ ID NO: 1, and the heavy chain variable region comprises the amino acid sequence set forth as SEQ ID NO: 2.

23. The method of claim 14, wherein the antibody is birtamimab.

24. The method of claim 14, wherein the patient is newly diagnosed and AL amyloidosis treatment naive.

25. The method of claim 14, wherein the selected patient previously received or concomitantly receives administration of melphalan, prednisone, dexamethasone, bortezomib, cyclophosphamide, lenalidomide, doxorubicin, doxycycline, daratumumab, autologous transplant, or a combination thereof.

26. The method of claim 14, wherein the selected patient previously received or concomitantly receives administration of Cyclophosphamide, Bortezomib and Dexamethasone (CyBorD).

27. A method of treating a patient with AL amyloidosis, comprising:
  (a) selecting a patient with AL amyloidosis having a 6 minute walk distance (6MWD)≥150 meters and an ejection fraction (EF)>50% at baseline for treatment with an antibody comprising a light chain variable region comprising three complementarity determining regions set forth as SEQ ID NOs: 3, 4 and 5, and a heavy chain variable region comprising three complementarity determining regions set forth as SEQ ID NOs: 6, 7 and 8; and
  (b) administering an effective dosage of the antibody to the selected patient.

28. A method of treating a patient with AL amyloidosis comprising:
  (a) selecting a patient having AL amyloidosis for treatment with an antibody comprising a light chain variable region comprising three complementarity determining regions set forth as SEQ ID NOs: 3, 4 and 5, and a heavy chain variable region comprising three complementarity determining regions set forth as SEQ ID NOs: 6, 7 and 8, if the patient has Mayo Stage IV AL amyloidosis, a 6 minute walk distance (6MWD)≥150 meters, and an ejection fraction (EF)>50% at baseline; and
  (b) administering an effective dosage of the antibody to the selected patient.

29. A method of reducing the risk of mortality in a patient with AL amyloidosis by at least 45%, comprising:
  (a) selecting a patient having AL amyloidosis for treatment with an antibody comprising a light chain variable region comprising three complementarity determining regions set forth as SEQ ID NOs: 3, 4 and 5, and a heavy chain variable region comprising three complementarity determining regions set forth as SEQ ID NOs: 6, 7 and 8 if the patient has:
    (i) Mayo Stage IV AL amyloidosis;
    (ii) a 6MWD of greater than or equal to 150 meters and an EF of more than 50% at baseline, or
    (iii) Mayo Stage IV AL amyloidosis and an EF of >50% at baseline; and
  (b) administering an effective dosage of the antibody to the selected patient.

30. The method of claim 29, wherein the risk of mortality is of all-cause mortality.

31. The method of claim 29, wherein the risk of mortality is of cardiac mortality.

32. The method of claim 29, wherein the antibody is birtamimab.

33. The method of claim 29, wherein the effective dosage of the antibody is administered from a pharmaceutical formulation comprising the antibody at a concentration within the range from about 1 mg/mL to about 100 mg/mL.

34. The method of claim 29, wherein the dosage is from about 0.5 mg/kg to about 30 mg/kg and the antibody is administered intravenously or subcutaneously at a frequency of from about weekly to about quarterly.

35. The method of claim 33, wherein the antibody is present at a concentration of about 50 mg/mL.

36. The method of claim 33, wherein the dosage is about 24 mg/kg and the antibody is administered intravenously every 28 days.

37. The method of claim 29, wherein the duration of the treatment is at least 9 months.

38. The method of claim 29, wherein the duration of the treatment is at least 12 months.

39. The method of claim 29, wherein the antibody is a Fab, Fab', F(ab')2, F(ab)c, Dab, nanobody, or Fv.

40. A method of improving a 6 minute walk distance (6MWD) in a patient having AL amyloidosis, comprising:
  (a) selecting a patient having AL amyloidosis for treatment with an antibody comprising a light chain variable region comprising three complementarity determining regions set forth as SEQ ID NOs: 3, 4 and 5, and a heavy chain variable region comprising three complementarity determining regions set forth as SEQ ID NOs: 6, 7 and 8 if the patient has a 6MWD≥150 meters and EF>50% at baseline, and
  (b) administering an effective dosage of the antibody to the selected patient.

41. The method of claim 40, wherein the AL amyloidosis is Mayo Stage IV AL amyloidosis.

42. The method of claim 40, wherein the antibody is birtamimab.

* * * * *